US011292813B2

(12) United States Patent
Keyser et al.

(10) Patent No.: US 11,292,813 B2
(45) Date of Patent: Apr. 5, 2022

(54) IRON COMPOSITIONS AND METHODS OF MAKING AND USING THE SAME

(71) Applicant: RENIBUS THERAPEUTICS, INC., Lantana, TX (US)

(72) Inventors: Donald Jeffrey Keyser, Southlake, TX (US); Alvaro F. Guillem, Lantana, TX (US); Richard A. Zager, Mercer Island, WA (US)

(73) Assignee: RENIBUS THERAPEUTICS, INC., Southlake, TX (US)

( * ) Notice: Subject to any disclaimer, the term of this patent is extended or adjusted under 35 U.S.C. 154(b) by 0 days.

(21) Appl. No.: 16/805,223

(22) Filed: Feb. 28, 2020

(65) Prior Publication Data
US 2020/0277325 A1    Sep. 3, 2020

Related U.S. Application Data

(60) Provisional application No. 62/812,028, filed on Feb. 28, 2019.

(51) Int. Cl.
| | | |
|---|---|---|
| *C07H 23/00* | (2006.01) |
| *A61K 9/00* | (2006.01) |
| *A61K 9/08* | (2006.01) |
| *A61P 13/12* | (2006.01) |
| *A61K 33/26* | (2006.01) |
| *A61K 31/409* | (2006.01) |

(52) U.S. Cl.
CPC ........... *C07H 23/00* (2013.01); *A61K 9/0019* (2013.01); *A61K 9/08* (2013.01); *A61K 31/409* (2013.01)

(58) Field of Classification Search
CPC .......... C07H 23/00; A61P 13/12; A61K 33/26
See application file for complete search history.

(56) References Cited

U.S. PATENT DOCUMENTS

| | | | |
|---|---|---|---|
| 6,174,442 B1 | 1/2001 | Geisser et al. | |
| 2005/0209187 A1* | 9/2005 | Newton | C07H 23/00 514/53 |
| 2015/0165070 A1* | 6/2015 | Kratz | A61K 9/5161 600/409 |

FOREIGN PATENT DOCUMENTS

| | | |
|---|---|---|
| DE | 862482 C | 1/1953 |
| DE | 19547356 A1 | 6/1997 |
| WO | 20180148217 A1 | 8/2018 |

OTHER PUBLICATIONS

Venofer, Venofer Iron Sucrose Injection, "https://www.venofer.com/pdfs/venofer-safety-data-sheet.pdf" (Year: 2019).*
International Search Report received in Application No. PCT/US2020/020517 dated Jun. 18, 2020, 2 pages.

* cited by examiner

*Primary Examiner* — Mark V Stevens
*Assistant Examiner* — Alparslan Asan
(74) *Attorney, Agent, or Firm* — Jeff B. Vockrodt; Culhane Meadows, PLLC

(57) ABSTRACT

The present invention involves a novel aqueous iron composition. The aqueous iron composition includes iron sucrose and bicarbonate. The aqueous iron composition of the invention exhibits enhanced renal protective effects relative to conventional iron sucrose compositions.

3 Claims, 25 Drawing Sheets

FIG. 19: 13C NMR spectra of S1-preparation 1

FIG. 20: 13C NMR spectra of S2-preparation 1

FIG. 21: 13C NMR spectra of S3-preparation 1

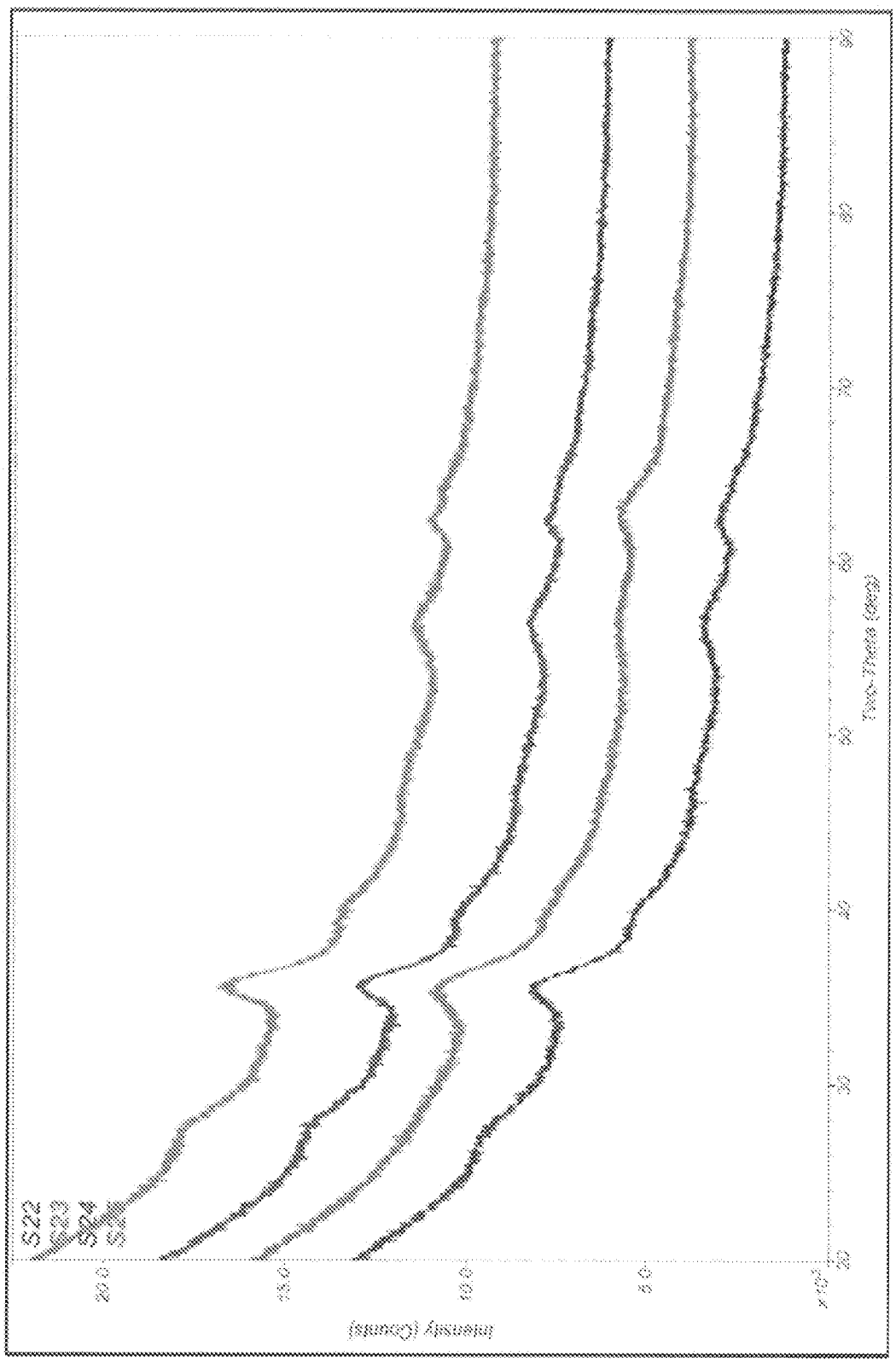
FIG. 23: Offset overlay of the data from all three samples (two replicates for S3)

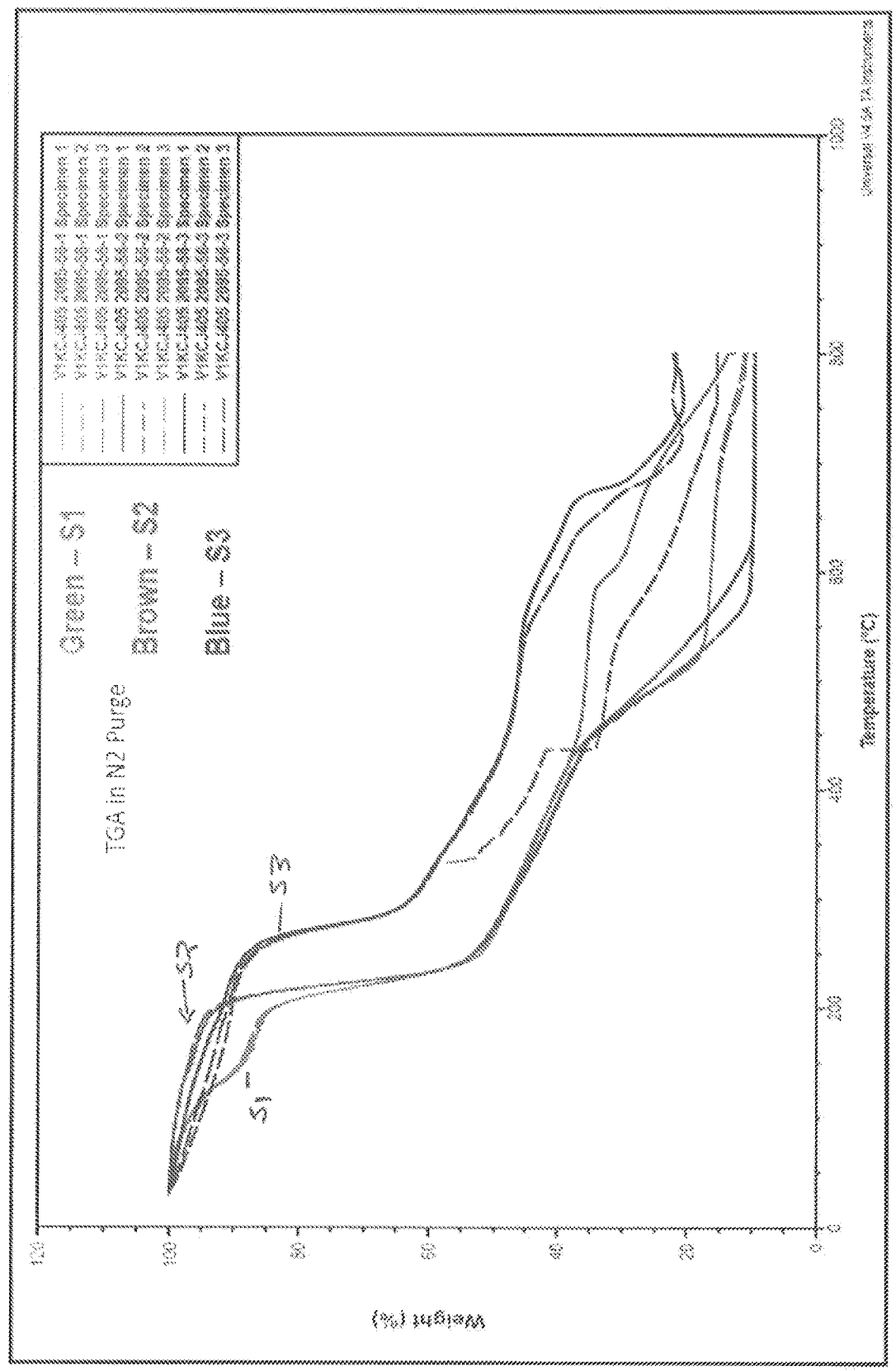
Fig. 24: TGA thermogram of S1, S2 and S3 under nitrogen purge condition

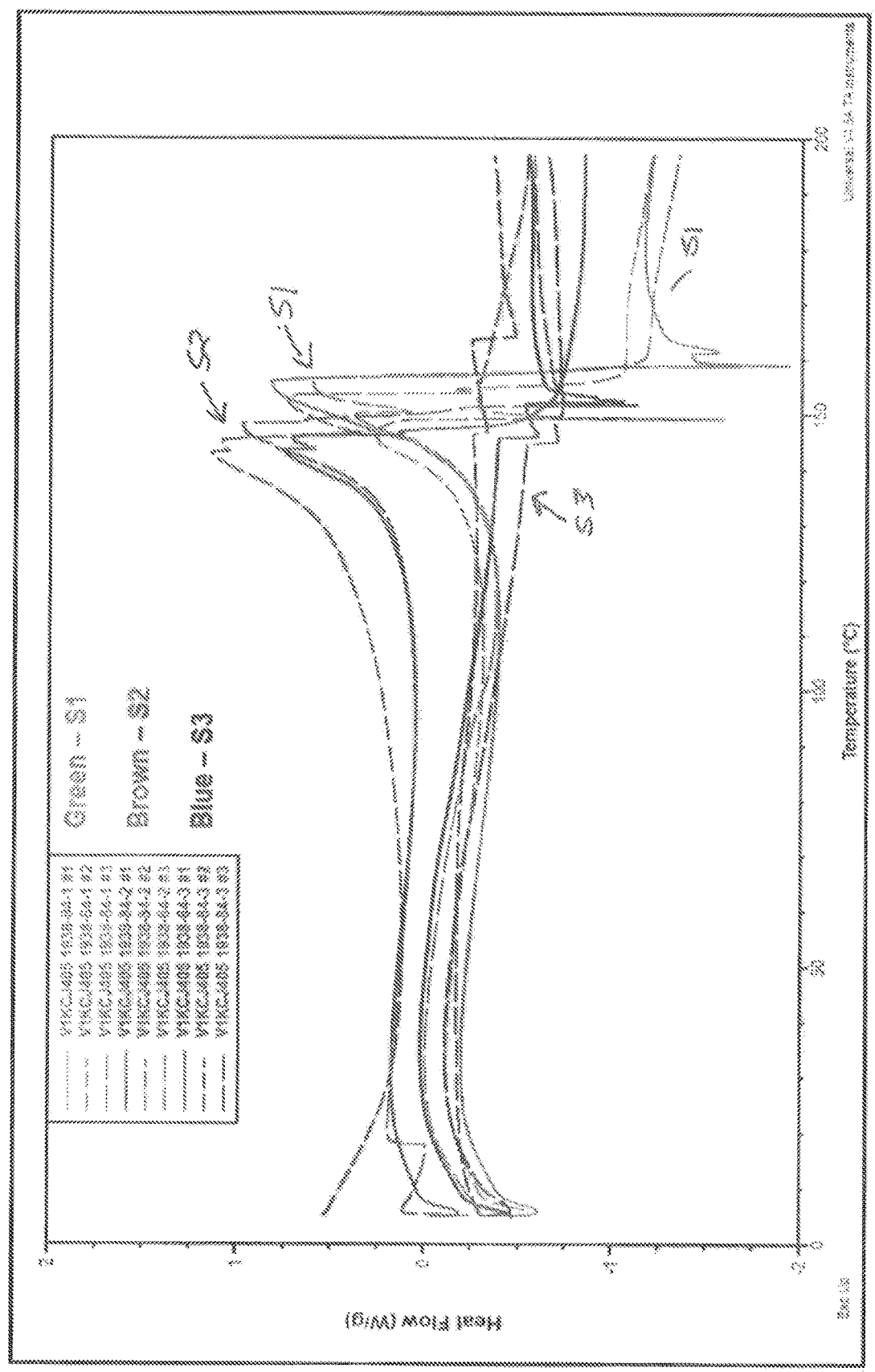
Fig. 25: DSC thermograms of S1, S2 and S3

IRON COMPOSITIONS AND METHODS OF MAKING AND USING THE SAME

This application claims priority to provisional application No. 62/812,028, filed Feb. 28, 2019, entitled Novel Iron Compositions and Methods of Marking and Using the Same, which is incorporated by reference herein in its entirety.

BACKGROUND OF THE INVENTION

The intravenous (IV) iron agents are colloids that consist of spheroidal iron-carbohydrate nanoparticles as shown in FIG. 1. At the core of each particle is an iron-oxyhydroxide gel and the core is surrounded by a shell of carbohydrate that stabilizes the iron-oxyhydroxide (the main function of the ligand is to stabilize the complex and to protect it against further polynuclearization).

Iron carbohydrate complexes behave as prodrugs, since the iron has to be released from the iron(III)-hydroxide core. According to the proposed mechanism, after administration, the stable (Type 1) complexes such as ferric carboxymaltose and iron dextran are taken up by endocytosis by macrophages of the reticuloendothelial system (RES). See Danielson, J. Structure, chemistry, and pharmacokinetics of intravenous iron agents. Am. Soc. Nephrol. 2004, 15, S93-S98.

In the case of less stable iron(III)-carbohydrates (Type 2), significant amounts of labile iron from the complex can be released and lead to saturation of transferrin and, thus, to significant amounts of non-transferrin bound iron (NTBI), particularly if high doses are administered. This weakly bound Fe3+ is readily taken up in an unregulated way by cells and can induce oxidative stress. Evans, R. W.; Rafique, R.; Zarea, A.; Rapisarda, C.; Cammack, R.; Evans, P. J.; Porter, J. B.; Hider, R. C. Nature of non-transferrin-bound iron: studies on iron citrate complexes and the thalassemic era. J. Biol. Inorg. Chem. 2008, 13, 57-74.

There are five types of injectable iron-carbohydrate products currently approved by the FDA (1) INFeD®/Dexferrum® (Iron dextran), Ferahem® (ferumoxytol), Injectafer® (ferric carboxymaltose), Venofer® (Iron sucrose), Ferrlecit® (Sodium ferric gluconate complex). Iron sucrose, sold under the name Venofer®, is formulated as a colloidal suspension having a molecular weight ($M_w$) of about 34,000-60,000 Daltons and a molecular formula as follows:

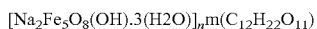

where n is the degree of iron polymerization and m is the number of sucrose molecules (C.sub.12 H.sub.22 O.sub.11) in complex with the poly-nuclear polymerized iron core:

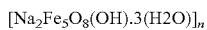

Each mL contains 20 mg elemental iron as iron sucrose in water for injection. Venofer® is available in 5 mL single dose vials (100 mg elemental iron per 5 mL) and 10 mL single dose vials (200 mg elemental iron per 10 mL). The drug product contains approximately 30% sucrose w/v (300 mg/mL) and has a pH of 10.5-11.1. The product contains no preservatives. The osmolarity of the injection is 1,250 mOsmol/L.

Methods for synthesizing iron carbohydrates are described in WO 97/11711 (1997) by Lawrence et al, which disclosed Ferric oxyhydroxide-dextran compositions for treating iron deficiency having ellipsoidal particles with a preferred molecular weight range of about 250,000 to 300,000 daltons.

Recently, iron sucrose has been used in combination with tin protoporphyrin (SnPP) to induce acquired cytoresistance without causing injury to the organ. See U.S. Pat. No. 9,844,563 to Zager et al. The present inventors have found a need for an iron sucrose formulation that can be easily combined with tin protoporphyrin (SnPP), that is stable, and can be injected into a patient to treat iron deficiency or for its renal protective effects either alone or in combination with another agent such as SnPP.

SUMMARY OF THE INVENTION

The invention relates to aqueous iron sucrose compositions having desirable properties. In one aspect, the aqueous irons sucrose composition comprises iron sucrose and bicarbonate. In one aspect, the invention relates to an aqueous iron pharmaceutical composition comprising: iron sucrose; bicarbonate; and a pharmaceutically acceptable aqueous carrier. In another aspect, the invention relates to a method for prevention or treatment of a kidney disease or disorder comprising intravenously administering an aqueous iron composition in a therapeutically effective amount, wherein the aqueous iron composition comprises iron sucrose and bicarbonate.

DESCRIPTION OF THE FIGURES

FIG. 23 shows Offset overlay of the data from all three samples (two replicates for 53).
FIG. 24 shows TGA thermogram of S1, S2 and S3 under nitrogen purge condition.
FIG. 25 shows DSC thermograms of S1, S2 and S3.

DETAILED DESCRIPTION OF THE INVENTION

Figure 1:
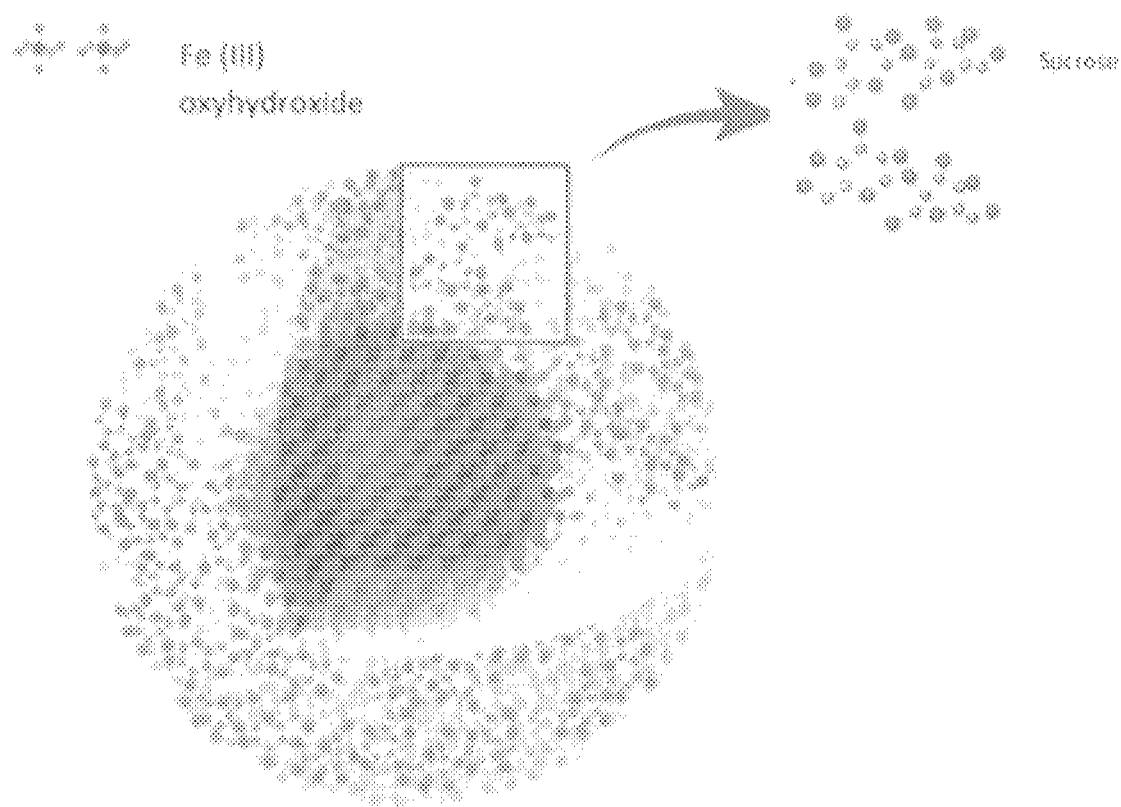
FIG. 1 shows the structure of an iron carbohydrate.

In one embodiment, the present invention involves an aqueous iron sucrose (FeS) and bicarbonate (FeS-bicarb)

composition. The present inventors have found that this composition has beneficial properties. In one respect, the FeS-bicarb composition of the present invention can be utilized as a renal protective agent. The inventors have discovered that the FeS-bicarb composition according to embodiments of the invention is preferentially absorbed in the kidney compared to commercially available forms of FeS. Further, the inventors have found that FeS-bicarb results in preferential upregulation of kidney protective molecule(s) relative to FeS alone. In another aspect, the FeS-bicarb composition of the present invention may be advantageously combined with other renal protective agents such as tin protoporphyrin (SnPP) to readily form injectable renal protective agents.

One advantage of using the FeS-bicarb is that this composition results in elevated renal protective effects. Specifically, the inventors found that FeS-bicarb preferentially upregulated kidney protective molecules relative to FeS alone. While not wishing to be bound by theory, the present inventors have proposed that the bicarb in addition to FeS may alter the relative levels of Fe(III) and Fe(II) present. Because of the observed redness in the FeS-bicarb product, the inventors have proposed that the compositions of the invention may include elevated levels of Fe(II). This could explain the elevated renal protective effects, given the higher reactivity of Fe(II) relative to Fe(III).

One advantage of using the FeS-bicarb is that the bicarb has a buffering effect. When using a tin protoporphyrin composition this can be advantageous since SnPP is best stored at low pH to prevent unwanted dimerization during storage. According to the present disclosure, the SnPP composition may be combined with the FeS-bicarb composition in a ratio of less than or equal to about 1:1 SnPP:FeS, such as about 1:2, about 1:4, about 1:8, about 1:10, about 1:20, about 1:50, about 1:100, about 1:1000, about 1:10,000, about 1:100,000, about 1:1,000,000, or any integer or subrange in between.

In one aspect, the composition has a molecular weight measured using GPC as described in Example 1. The Mp is preferably within the range of between 25,000 and 35,000 Daltons, more preferably between 28,000 and 32,000 Daltons, and most preferably about 29,000 Daltons. The Mw is preferably within the range of between 25,000 and 45,000 Daltons, more preferably between 30,000 and 40,000 Daltons, even more preferably between 33,000 and 38,000 Daltons, and most preferably about 34,000 Daltons. The Mn is preferably within the range of between 15,000 and 30,000 Daltons, more preferably between 20,000 and 25,000 Daltons, and most preferably about 24,000 Daltons. The polydispersity (PDI) is preferably within the range of 1.35 to 1.60, more preferably within the range of 1.38 and 1.5, even more preferably within the range 1.40 and 1.48, and most preferably about 1.4.

In one aspect, the composition has a stable zeta potential of −3.0 mV or less, more preferably −7.0 mV or less, and most preferably around −10 mV. In one aspect, the composition has a total organic carbon of less than 8.5%, preferably less than 8.0%, and most preferably about 7.7%. In one aspect, the osmolality as measured in accordance with Example 1 is within the range of 550 and 1600 mOsm/kg, preferably within the range of 1500 and 1580 mOsm/kg, and most preferably about 1540 mOsm/kg.

Example 1

The present invention involves a composition that is prepared by dissolving enough iron sucrose complex in water (ca 3.5 L) to give a 12 mg/mL (expressed as iron) solution when diluted to 6.0 L. The amount of iron sucrose needed was calculated for the final volume of liquid, 6100 mL (6.1 L) so that the final concentration is 12 mg/mL. This requires 73.2 g of iron. The use potency of iron sucrose is 0.0550. Thus, 73.2 g/0.0550 or 1331 g±1 g of iron sucrose is needed. Iron sucrose, 1331 g±1 g, was weighed directly into a 6.0 L Erlenmeyer flask. Approximately 3-3.5 L of water is added to the Erlenmeyer flask, and the contents of the flask are stirred.

Sodium bicarbonate is added in an amount such that the final sodium bicarbonate concentration is 10 mg/ml when diluted to 6.0 L. Sodium bicarbonate, 109.8±0.1 g, is weighed and added to the 6.0 L flask.

Sodium chloride is added in an amount such that the final sodium chloride concentration is 9.0 mg/mL upon dilution. Sodium chloride, 54.9±0.1 g, is weighed and added to the 6.0 L flask. The suspension is stirred for 30-120 minutes to give a black opaque solution.

The pH of the solution is monitored with a pH meter while 1M sodium hydroxide is added in small portions until pH 10.30 is reached and remains stable. Sodium hydroxide, 40.0±0.1 g, was added to a 1.0 L Erlenmeyer flask. 1.0±0.1 L of water is added to the 1.0 L Erlenmeyer flask and stirred until all of the sodium hydroxide dissolved. A pH probe is affixed to monitor the pH of the 6.0 L Erlenmeyer flask and the sodium hydroxide is added in <100 mL portions until the pH=10.3±0.1. The solution is then stirred for 10 minutes. The pH is checked again after 10 minutes and if necessary adjusted to within pH=10.3±0.1.

The solution is then transferred to a volumetrically accurate flask and diluted to 6.1 L with water. A 2 L volumetric flask is used twice to transfer exactly 4 L of the 10.3 pH solution to a 6 L Erlenmeyer flask. The remaining 10.3 pH solution is diluted to 2 L in a volumetric flask and added to the 6 L Erlenmeyer flask. The 100 mL graduated cylinder is used to add 100±0.1 mL to the 6.0 L Erlenmeyer, and the resulting solution is stirred for 10 minutes.

The resulting product solution appears dark red to brown. Two isotopes of iron are present in the sample preparation in a ratio consistent with that of the standard preparation. The resulting material had a pH of 10.3, which is within the preferred limits of 10.1-10.4. The resultant material had 11.5/11.6 parts per thousand (mg/mL) iron according to SOP 174472, which determines iron through inductively coupled plasma-mass spectroscopy.

Additional properties of the resultant composition are found in Table 1 below:

TABLE 1

| | Properties of the Composition of Example 1 | | |
|---|---|---|---|
| Test | Observation/ Results | Specification | Reference to Test Method |
| Description | Brown to dark brown powder | Brown to dark brown powder | In house |

TABLE 1-continued

Properties of the Composition of Example 1

| Test | Observation/ Results | Specification | Reference to Test Method |
| --- | --- | --- | --- |
| Solubility | Freely soluble in water. Practically insoluble in methanol | Freely soluble in water. Practically insoluble in methanol | |
| Identification | | | |
| Iron | Red color discharge | Red color should discharge | USP38 Monographs of Iron sucrose Injection |
| Sucrose | Complies | The retention time of major peak in chromatogram of Assay Preparation corresponds to that in chromatogram of Standard Preparation, as obtained in the assay for sucrose. | USP38 Monographs of Iron sucrose injection. |
| Molecular Weight | | | |
| Mw | 52149 Da | Between 34000 and 60000 Da | USP 38 Monographs of Iron sucrose Injection_Method Validate |
| Mn | 35897 Da | Not Less Than 24000 Da | |
| Mw/Mn | 1.453 | Not more than 1.70 | |
| pH | 11.04 | Between 10.50 and 11.0 | USP38<791>Monograph of Iron sucrose injection |
| Specific Gravity | 1.156 | Between 1.135 and 1.165 at 20° C. | USP38<841> Monograph of Iron sucrose injection |
| Turbidity | At 4.67 pH | pH Between 4.40 and 5.30 | USP38 Monograph of Iron Sucrose Injection |
| Alkalinity | 0.68 mL | Between 0.5 mL and 0.8 mL of 0.1N Hydrochloric Acid consumed per mL. | USP38 Monograph of Iron Sucrose Injection |
| Limit of Iron (II) | 0.16% w/v | Not more than 0.40% w/v | USP38 Monograph of Iron Sucrose Injection |
| Low Molecular Weight Fe(II) and Fe(III) complexes | No additional peaks in polarograms of Limit of Iron (II) observed | No additional peaks in polarograms of Limit of Iron (II) should be observed | USP38 Monograph of Iron Sucrose Injection |
| Content of Chloride | 0.013% w/w | Between 0.012% w/w and 0.025% w/w | USP 38 Monographs of Iron sucrose Injection_Method Validate |
| Assay of Sucrose (by HPLC) | 85.21% w/w | Between 80.00% (w/w) and 90.00% (w/w) on a dried basis | USP 38 Monographs of Iron sucrose Injection_Method Validate |
| Total Iron (III) Assay (by AAS) | 5.66% w/w | Between 5.00% w/w/ and 6.00% w/w/ on a dried basis. | USP 38 Monographs of Iron sucrose Injection |
| Loss on Drying | 1.24% w/w | Not More Than 5.00% w/w | USP38 |
| Heavy Metals | | | |
| Arsenic | Less than 2.0 ppm | Not more than 2.0 ppm | In House |
| Copper | Less than 20 ppm | Not more than 20 ppm | In House |
| Lead | Less than 20 ppm | Not more than 20 ppm | In House |
| Residual Solvents | Methanol: 2624.41 ppm | Methanol: NMT 3000 ppm | USP 38<467> |
| | Acetone: 366 ppm | Acetone: NMT 5000 ppm | USP 38<467> |
| Osmolarity | 1220 mOsmol/Lit | Between 1150 and 1350 mOsmol/Lit. | USP38<785> Monographs of Iron Sucrose Injection |
| Particulate Matter | 54.66 | ≤10 μm 6000 per container | USP38<785> Monographs of Iron Sucrose Injection |
| | 1.66 | ≤25 μm 600 per container | USP38<785> Monographs of Iron Sucrose Injection |
| Bacterial Endotoxin | Less Than 3.70 EU/mg of Iron | Not More Than 3.7 EU/mg of Iron | USP38<785> Monographs of Iron Sucrose Injection |

TABLE 1-continued

Properties of the Composition of Example 1

| Test | Observation/ Results | Specification | Reference to Test Method |
|---|---|---|---|
| Microbial Limit | | | |
| Total Aerobic Bacteria | 20 CFU/g | Not More Than 100 CFU/g | USP38<61> |
| Total Yeast & Mold | Less Than 10 CFU/g | Not More Than 10 CFU/g | |
| Enterobacteriaceae count | Less Than 10 CFU/g | Not More Than 10 CFU/g | |
| Total *E. Coli* | Absent | Should be Absent | |
| *Stapha. Aureus* | Absent | Should be Absent | |
| *Pseudomonas Aeruginosa* | Absent | Should be Absent | |
| *Salmonella* | Absent | Should be Absent | |

The resulting FeS-bicarb composition has the following stoichiometry and physical constants are shown in Table 2 below:

TABLE 2

Stoichiometry and Physical Constants

| Reagent | MW | Percentage Active | Nominal Amount |
|---|---|---|---|
| Iron Sucrose | 736 | 5.5 | 1331 g |
| Sodium Bicarbonate | 84 | 100 | 110 g |
| Sodium Chloride | 58 | 100 | 55 g |
| Sodium Hydroxide | 40 | 100 | 39 g |
| Water | 46.07 | 1000 | 6.1 L |

Example 2

The intravenous administration of the iron sucrose (FeS) bicarb composition of Example 1 was conducted for 4 hours and resulted in elevated renal heme oxygenase 1 (HO-1) relative to commercially available iron sucrose (FeS) composition sold under the brand name, Venofer®. The results are shown in Table 3 below.

TABLE 3

Kidney mRNA HO-1/GAPDH

| Run # | Control | 4 hr IV FeS, Venofer® | 4 hr IV FeS-bicarb |
|---|---|---|---|
| 1 | 0.22 | 1.52 | 3.2 |
| 2 | 0.04 | 1.23 | 2.01 |
| 3 | 0.06 | 1.11 | 1.99 |
| 4 | 0.07 | 2.23 | 2.23 |
| 5 | | 1.86 | 1.86 |
| Average | 0.1 | 1.59 | 2.34 |
| Std. Err | 0.04 | 0.21 | 0.23 |

The elevated level of HO-1 observed in the kidney was not observed in the liver. Instead, the level of HO-1 was not observed to be increased for FeS-bicarb relative to what was observed for Venofer®. The results are shown in Table 4 below.

TABLE 4

Liver mRNA HO-1/GAPDH

| Run # | Control | 4 hr IV FeS, Venofer® | 4 hr IV FeS-bicarb |
|---|---|---|---|
| 1 | 0.09 | 0.99 | 0.49 |
| 2 | 0.13 | 1.06 | 0.36 |
| 3 | 0.11 | 0.51 | 0.93 |
| 4 | 0.08 | 1.24 | 0.92 |
| 5 | | 1.07 | 0.49 |
| Average | 0.1 | 0.97 | 0.64 |
| Std. Err | 0.01 | 0.12 | 0.12 |

The plasma BUN and Creatinine were similar for both FeS, Venofer® and FeS-bicarb as shown in Tables 5 and 6 below.

TABLE 5

BUN - Plasma

| Run # | Control | 4 hr IV FeS, Venofer® | 4 hr IV FeS-bicarb |
|---|---|---|---|
| 1 | 28 | 20 | 23 |
| 2 | 22 | 18 | 23 |
| 3 | 23 | 22 | 22 |
| 4 | 35 | 25 | 24 |
| 5 | | 25 | 28 |
| Average | 27 | 22 | 24 |

TABLE 6

Creatinine - Plasma

| Run # | Control | 4 hr IV FeS, Venofer® | 4 hr IV FeS-bicarb |
|---|---|---|---|
| 1 | 0.32 | 0.27 | 0.34 |
| 2 | 0.31 | 0.29 | 0.31 |
| 3 | 0.31 | 0.28 | 0.31 |
| 4 | 0.31 | 0.25 | 0.32 |
| 5 | | 0.32 | 0.30 |
| Average | 0.31 | 0.28 | 0.32 |

Example 3

FeS-bicarb composition of Example 1 was filtered and placed in a vial and had a FeS concentration of 12 mg/mL (CoreRx Lot #111002-18011). The osmolarity of this 12 mg/mL solution was 831 mOsm. For Venofer® Iron Sucrose Injection 20 mg/mL, American Regent, Lot #8243A, the osmolarity was 1742 mOsm. These osmolarity measurements were made without dilution.

Example 4

Figure 2:
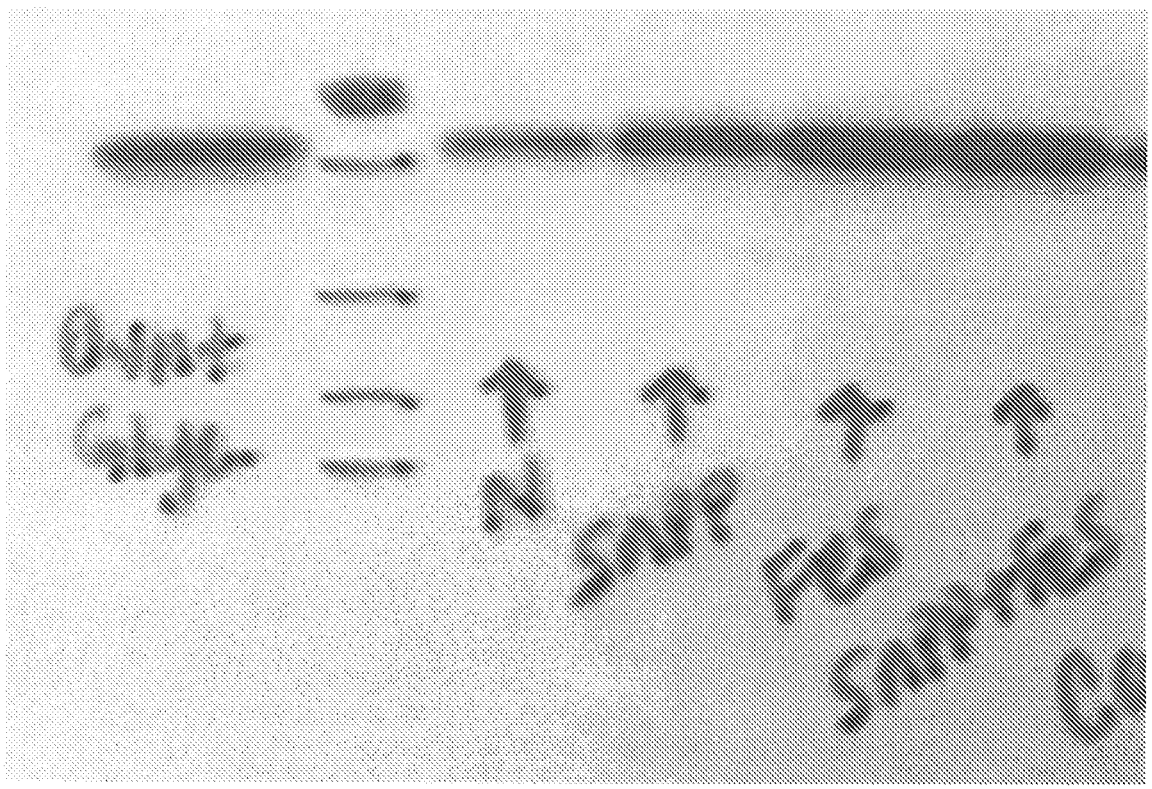
FIG. 2 is a Western blot of kidney at 18 hours post administration of aqueous iron compositions.
Figure 3:
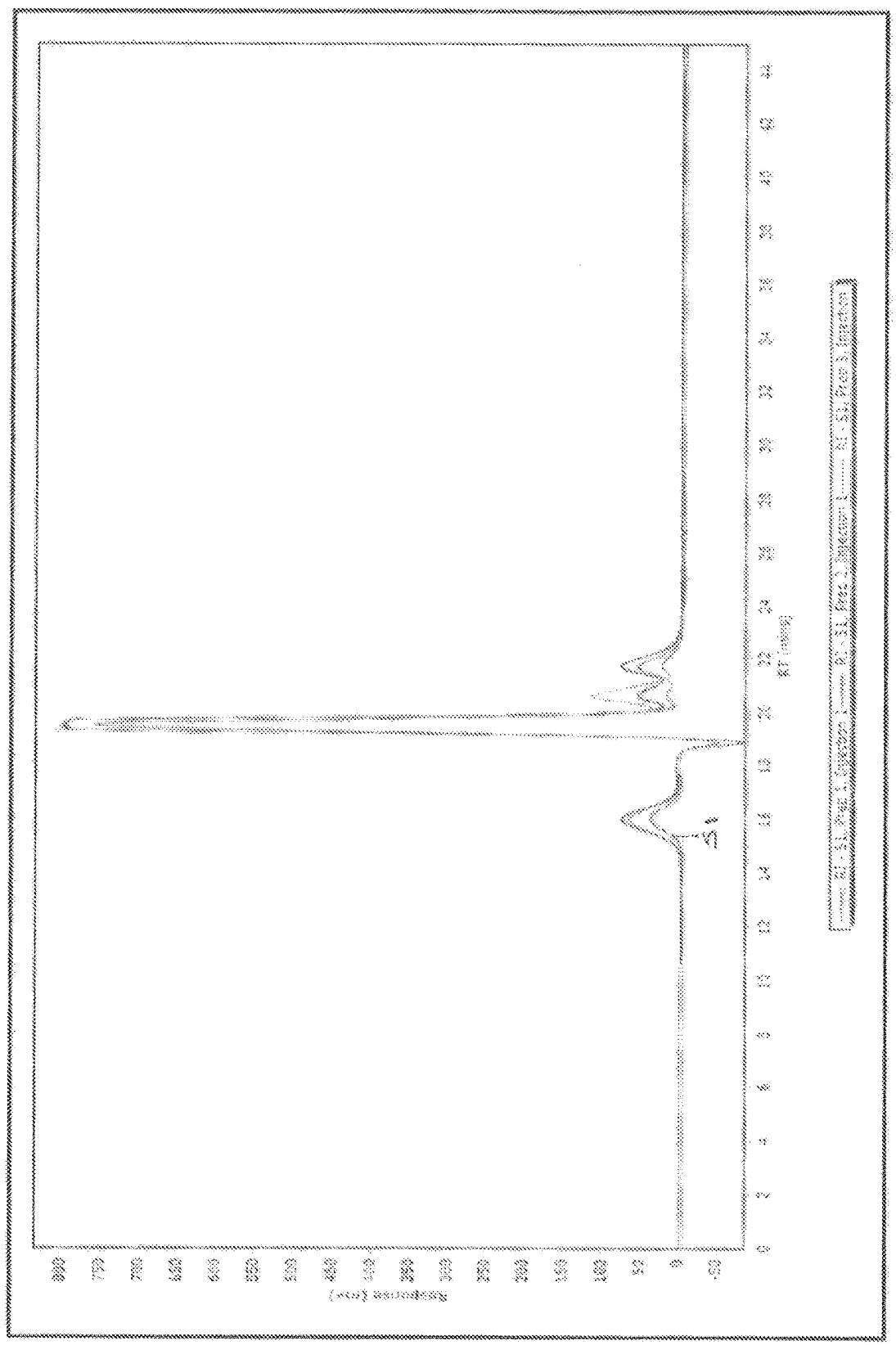
FIG. 3 shows GPC chromatograms of three S1 preparations.
Figure 4:
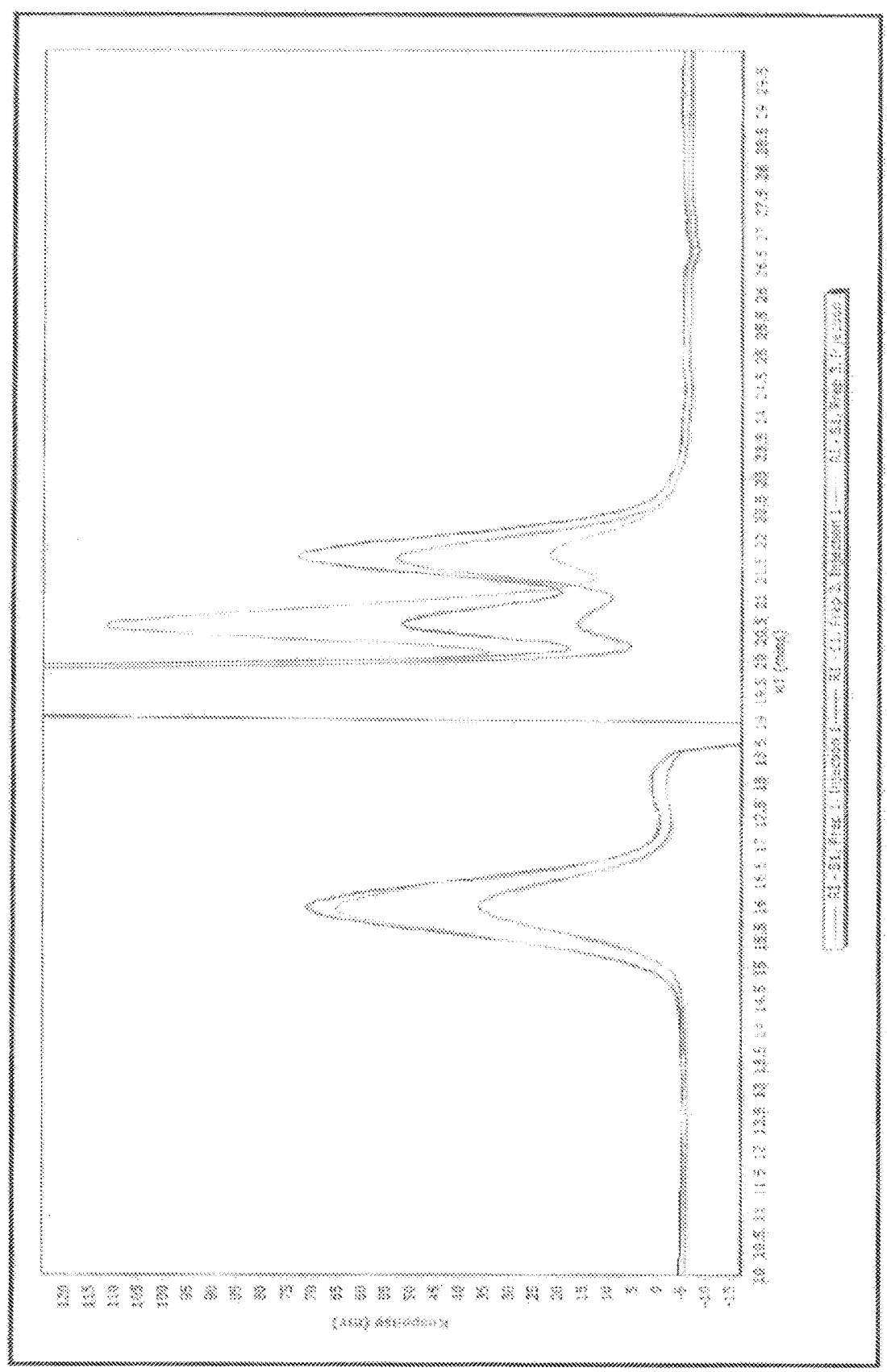
FIG. 4 shows a zoom view of FIG. 3.
Figure 5:
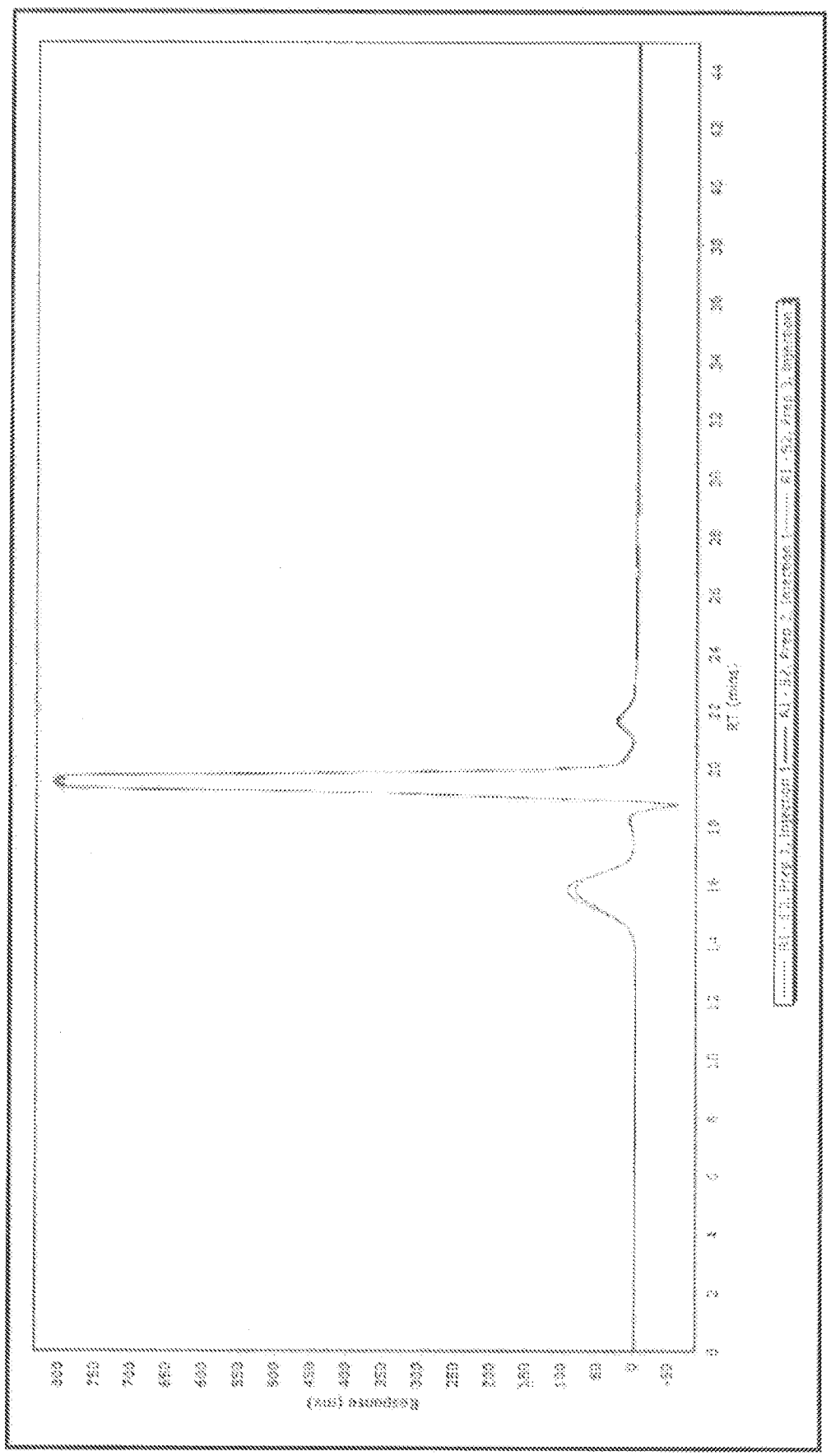
FIG. 5 shows GPC chromatograms of three S1 preparations.
Figure 6:
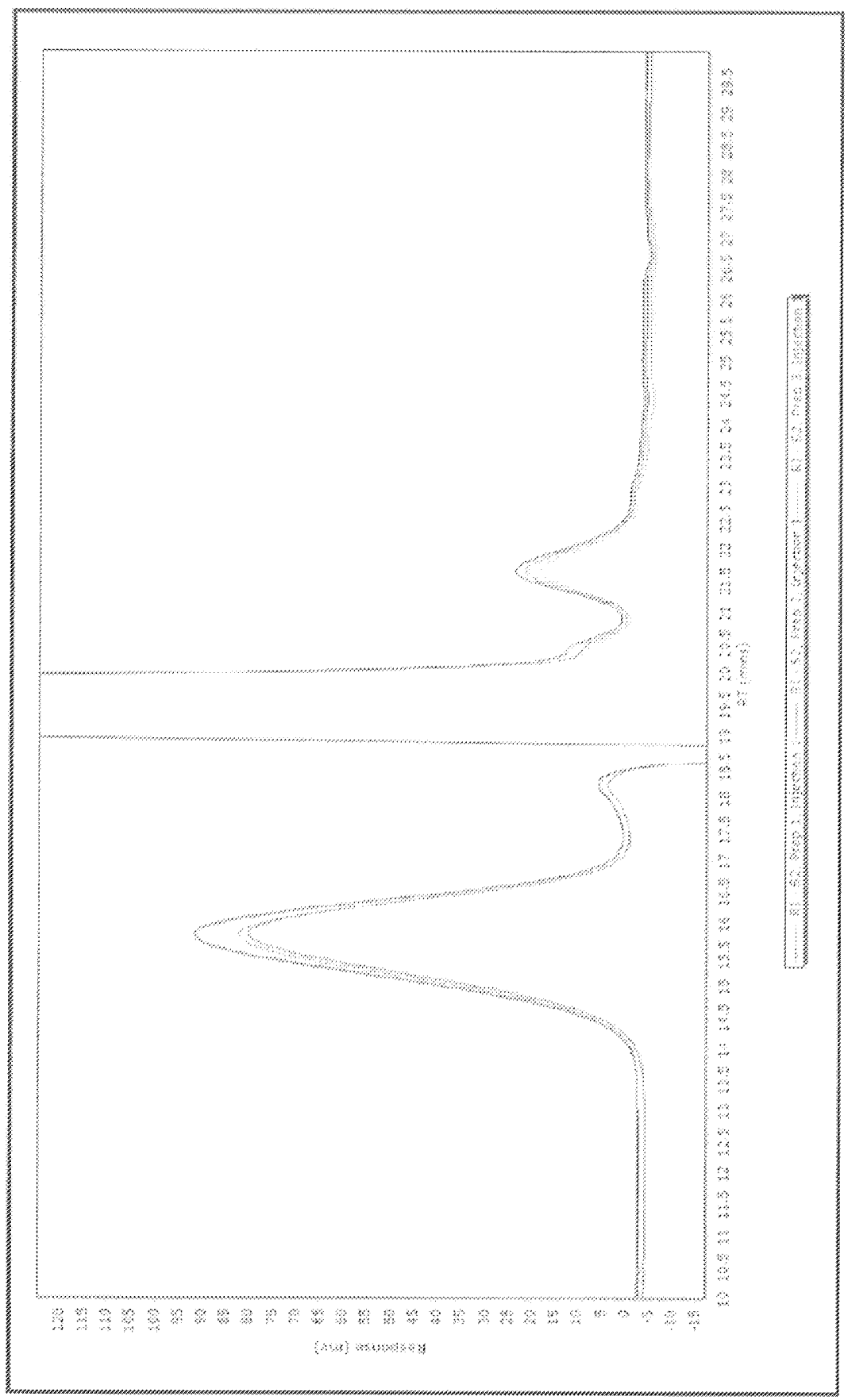
FIG. 6 shows a zoom view of FIG. 5.
Figure 7:
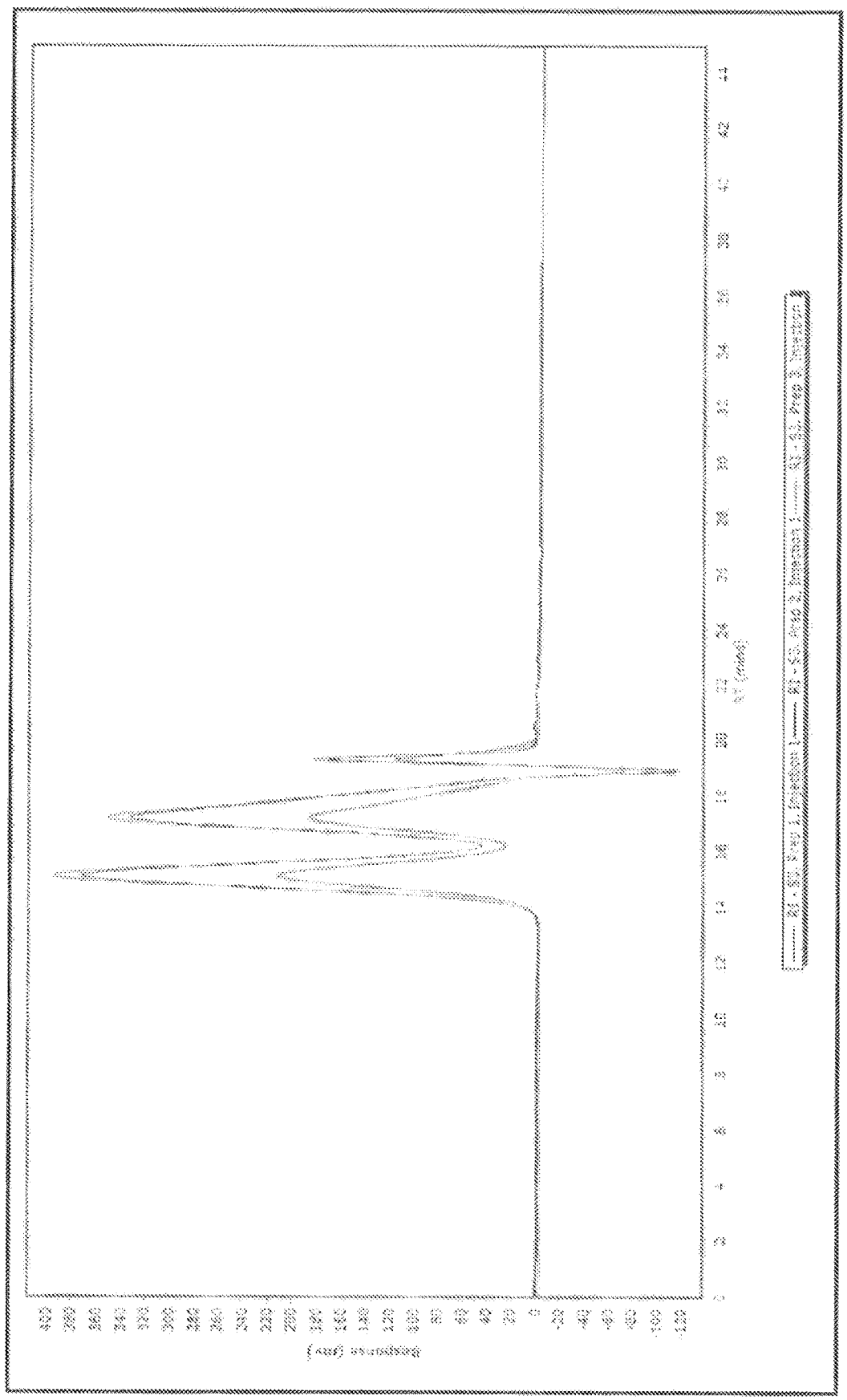
FIG. 7 shows GPC chromatograms of three S1 preparations.
Figure 8:
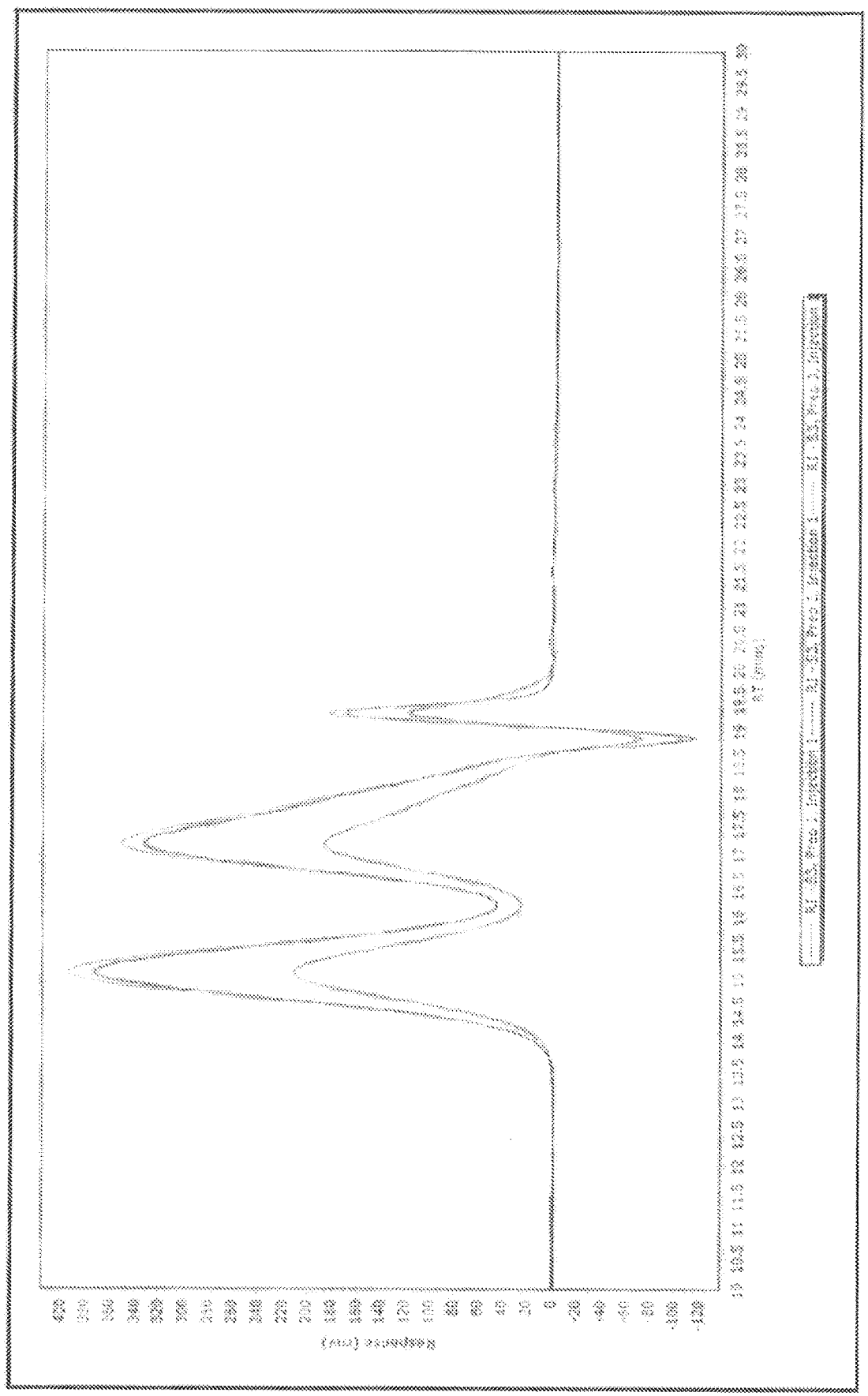
FIG. 8 shows a zoom view of FIG. 7.
Figure 9:
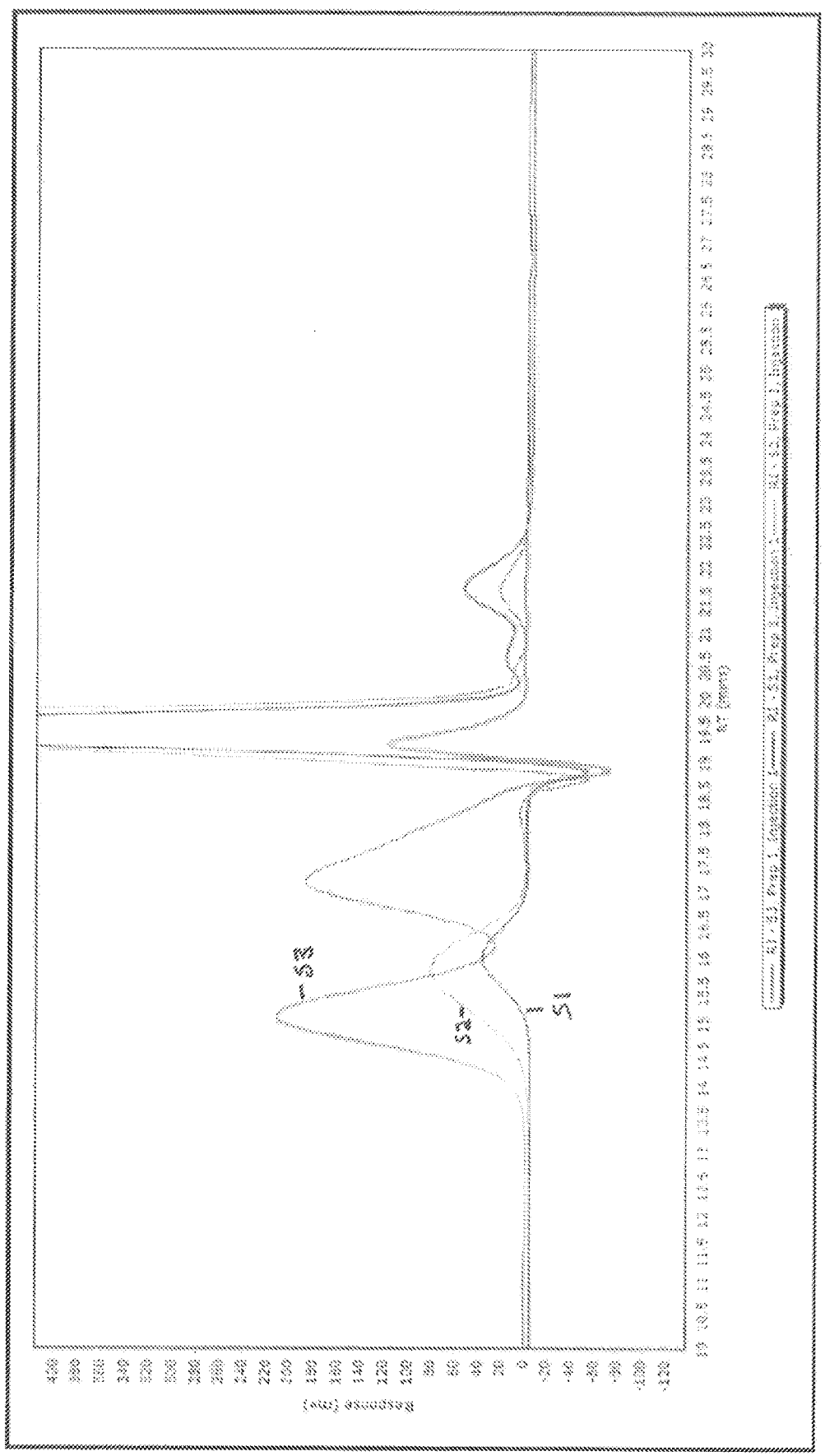
FIG. 9 shows a comparison of GPC for S1, S2, and S3.

A Western blot of kidney at 18 hours post administration of aqueous iron compositions is shown in FIG. 2 and Table 7:

TABLE 7

|  | Normal | Venofer | RBT3 |
|---|---|---|---|
| Kidney |  |  |  |
| HO-1 mRNA | 0.1 ± 0.04 | 1.59 ± 0.21 <0.001 | 2.34 ± 0.23 <0.001 (<0.05) |
| Ftn LC mRNA | 1.10 ± 0.06 | 1.36 ± 0.04 <0.01 | 1.47 ± 0.09 <0.02 (NS) |
| Ftn HC mRNA | 1.38 ± 0.01 | 1.38 ± 0.03 NS | 1.49 ± 0.06 NS (<0.05)* |
| Liver |  |  |  |
| HO-1 mRNA | 0.10 ± 0.01 | 0.97 ± 0.012 <0.001 | 0.64 ± 0.12 <0.01 (0.085) |
| Ftn LC mRNA | 3.65 ± 0.15 | 4.02 ± 0.1 NS | 3.63 ± 0.13 NS |
| Ftn HC mRNA | 1.77 ± 0.11 | 1.82 ± 0.1 NS | 1.71 ± 0.14 NS |

On the left, is a heavy chain specific Western blot of kidney at 18 hr post SnPP, FeS (Venofer) or Fe+SnPP. N=normal control. Glyc is glycerol, used as a positive H chain ferritin control. N=normal samples (controls). As is apparent, Fe induces an increase in heavy chain in kidney.

Example 5

A patient suffering from chronic kidney disease is treated by intravenous injection using the aqueous iron composition of iron sucrose and bicarbonate of Example 1.

Example 6

A patient undergoing organ transplantation is treated by intravenous injection using the aqueous iron composition of iron sucrose and bicarbonate of Example 1.

Example 7

A patient undergoing organ transplantation is treated by intravenous injection using the aqueous iron composition of iron sucrose and bicarbonate of Example 1, in combination with tin protoporphyrin.

Example 8

Three samples of iron-sucrose (S1, S2) and iron-dextran (S3) were characterized by a variety of analytical techniques. S1 was prepared in accordance with Example 1 above. S2 is the commercially available product, Venofer® (iron sucrose injection). S3 is the commercially available product INFeD® (iron dextran injection). The results are summarized in Table 8 below.

TABLE 8

Comparison of Example 1 to Venofer ® and INFeD ®

| | ANALYSIS | | S1 FES STERILE LIQUID 5 ML UNLABELED VIAL (6R) LOT: AK2087 | | S2 VENOFER (IRON SUCROSE INJECTION, USP) (20 mg/mL) Lot: 9043 | | S3 INFED (IRON DEXTRAN INJECTION, USP) (50 mg/mL) Lot: 18W11A | |
|---|---|---|---|---|---|---|---|---|
| GPC | $M_p$ | | 29,239 | | 35,709 | | 83,090 | |
| | $M_w$ | | 34,355 | | 50,855 | | 92,838 | |
| | $M_n$ | | 23,881 | | 31,345 | | 70,640 | |
| | PDI | | 1.44 | | 1.62 | | 1.31 | |
| DLS | Z average | | 15.30 nm | | 15.41 nm | | 16.88 nm | |
| | PDI | | 0.32 | | 0.31 | | 0.21 | |
| Zeta Potential | Zeta Potential | | −10.16 mV | | No stable reading obtained | | −2.61 mV | |
| | Zeta Potential Temp. | | 25.0° C. | | | | 25.0° C. | |
| | pH | | 10.70 | | | | 10.23 | |
| | pH Temp. | | 25.0° C. | | | | 22.2° C. | |
| AFM | Location | | 1 | 2 | 1 | 2 | 1 | 2 |
| | Mean Height | | 2.38 nm | 2.43 nm | 3.88 nm | 3.49 nm | 4.20 nm | 3.23 nm |
| | Min Height | | 1.34 nm | 1.16 nm | 0.99 nm | 1.20 nm | 1.19 nm | 0.91 nm |
| | Max Height | | 3.62 nm | 3.73 nm | 8.35 nm | 7.76 nm | 10.19 nm | 7.23 nm |
| | σ | | 0.61 | 0.73 | 1.53 | 1.33 | 1.46 | 1.47 |
| | # Particles | | 21 | 29 | 84 | 52 | 117 | 49 |
| TOC | | | 7.69% | | 12.14% | | 8.69% | |
| Osmolality | | | 1540 mOsm/kg | | 1681 mOsm/kg | | 529 mOsm/kg | |
| $Fe^{3+}$ vs $Fe^{2+}$ | Fe(II) | | 0.41 mg/mL | | 3.16 mg/mL | | 0.44 mg/mL | |
| | Fe(III) | | 11.43 mg/mL | | 16.90 mg/mL | | 50.90 mg/mL | |
| | Total Fe | | 11.87 mg/mL | | 20.02 mg/mL | | 51.33 mg/mL | |
| | % Fe(II) | | 3.4% | | 15.8% | | 0.8% | |
| ICP-OES | Total Fe | | 1.07 wt % | | 1.77 wt % | | 4.51 wt % | |
| | Total Na | | 1.26 wt % | | 0.50 wt % | | 0.42 wt % | |
| ICP-MS Screen for Additional Elements | Summary | | No element found >50 ppm, see report body for more | | No elements found >80 ppm, see report body for | | No elements found >30 ppm, see report body for more | |
| | Highest Conc. Element | | Si, 50 ppm | | Si, 80 ppm | | Si, 30 ppm | |

TABLE 8-continued

Comparison of Example 1 to Venofer ® and INFeD ®

| ANALYSIS | | | S1 FES STERILE LIQUID 5 ML UNLABELED VIAL (6R) LOT: AK2087 | | S2 VENOFER (IRON SUCROSE INJECTION, USP) (20 mg/mL) Lot: 9043 | | S3 INFED (IRON DEXTRAN INJECTION, USP) (50 mg/mL) Lot: 18W11A | |
|---|---|---|---|---|---|---|---|---|
| Chemical Family by FT-IR | | | Sucrose | | Sucrose | | Dextran | |
| NMR Spectroscopy | NMR | | Broad peaks observed, chemical shifts are consistent with dextran | | Very broad peaks observed, chemical shifts are consistent with sucrose | | Broad peaks observed, chemical shifts are consistent with dextran | |
| | $^{13}C$ NMR | | Peaks are consistent with sucrose | | Peaks are consistent with sucrose, though slightly more broad than S1 | | Peaks are consistent with dextran | |
| XRD (lyophilized material) | | | Phases Detected | wt % | Phases Detected | wt % | Phases Detected | wt % |
| | | | $Na_4Fe_2O_5$—Sodium Iron Oxide Monoclinic, SG: P21/n (14) PDF# 04-013-8809 | 5.2 | $C_{12}H_{22}O_{11}$—Sucrose Monoclinic, S.G.: P21 (4) PDF# 02-063-8998 | 42.9 | $Na_4Fe_2O_5$—Sodium Iron Oxide Monoclinic, SG: P21/n (14) PDF# 04-013-8809 | 18.8 |
| | | | Amorphous materials | 94.8 | Amorphous materials | 57.1 | Amorphous materials | 81.2 |
| XRD (material purified with MWCO to remove sugars) | | | Phases Detected | wt % | Phases Detected | wt % | Phases Detected | wt % |
| | | | $Fe_{2.67}O_4$—Maghemite Cubic, SG: P4332 (212) PDF# [04-021-3968] | 81.0 | $Fe_{2.67}O_4$—Maghemite Cubic, SG: P4332 (212) PDF# [04-021-3968] | 89.9 | $Fe_{2.67}O_4$—Maghemite Cubic, SG: P4332 (212) PDF# [04-021-3968] | 74.0 |
| | | | FeOOH—Iron Oxide Hydroxide Orthorhombic PDF# [04-003-2900] | 19.0 | FeOOH—Iron Oxide Hydroxide Orthorhombic PDF# [04-003-2900] | 10.1 | FeOOH—Iron Oxide Hydroxide Orthorhombic PDF# [04-003-2900] | 26.0 |
| Acid Degradation for Labile Iron (III) | | | 1.48% | | 2.27% | | 1.34% | |
| TGA | Temp. | Cond. | | | Weight Loss (%) | | | |
| | RT to 100° | Nit. Air | 3.4 2.5 | | 1.1 0.9 | | 3.7 4.7 | |
| | 100° C. to 245° | Nit. Air | 42.7 43.2 | | 45.0 43.0 | | 8.2 7.8 | |
| | 245° C. to 530° | Nit. Air | 30.2 37.4 | | 35.4 45.1 | | 47.1 63.0 | |
| | 245° C. to 530° | Nit. Air | 11.8 5.7 | | 8.7 0.7 | | 20.8 3.0 | |
| | Residue at 800° C. | Nit. Air | 12.0 11.2 | | 9.8 10.3 | | 20.0 21.4 | |
| | | | | | Thermal Transitions Observed | | | |
| DSC | $Texo_1$ (° C.) | | 33.8 | | 29.2 | | 39.2 | |
| | $\Delta Hexo_1$ (J/g) | | 88.0 | | 47.6 | | 99.9 | |
| | $Texo_2$ (° C.) | | 154.9 | | 144.6 | | N/A | |
| | Onset $Texo_2$ (° C.) | | 141.0 | | 127.1 | | N/A | |
| | $\Delta Hexo_2$ (J/g) | | 171.7 | | 148 | | N/A | |

Finally, the as-received sample S1 was titrated in triplicate with dilute HCl to determine the hydroxide value in iron-sucrose injectable solution. The end points of the titrations were pH=7.0. Using the assumption that all basic species titrated were from the hydroxide associated with the ferric oxyhydroxide cores, the total number of moles of $H^+$ used in the titration was assumed to be equal to the number of moles of $OH^-$. Considering TOC, and Mw (or Mn) by GPC, the molecular formula of iron sucrose in S1 was calculated as below:

Mw based calculation: [Na6Fe5O8(OH)5.3H2O]13.73 (C12H22O11) Mn based calculation: [Na6Fe5O8(OH)5.3H2O]9.51(C12H22O11). Table 9 below shows details of the sample preparation and identification.

TABLE 9

Sample Preparation and Identification

| SAMPLE NUMBER | DESCRIPTION | DATE RECEIVED |
|---|---|---|
| S1 | FeS Sterile Liquid 5 mL Unlabeled Vial (6R) Lot: AK2087 Quantity: 15 | 11 Jul. 2019 |
| S2 | Venofer (Iron Sucrose Injection, USP) 100 mg Elemental Iron per 5 mL (20 mg/mL) Lot: 9043 Exp: FEB 21 (2 Each of 10 × 5 mL) | 11 Jul. 2019 |
| S3 | INFeD (Iron Dextran Injection, USP) 100 mg Elemental Iron/2 mL (50 mg/mL) Exp: October 2021 Lot: 18W11A (4 Each of 10 × 2 mL) | 11 Jul. 2019 |

Sample Preparation:

The samples were lyophilized to a dried residue prior to analysis unless otherwise stated.

Gel Permeation Chromatography (GPC):

GPC is used to determine the molecular weight distribution of polymers. In GPC analysis, a solution of the polymer is passed through a column packed with a porous gel. The sample is separated based on molecular size with larger molecules eluting quicker than smaller molecules. The retention time of each component is detected and compared to a calibration curve, and the resulting data is then used to calculate the molecular weight distribution for the sample.

A distribution of molecular weights rather than a unique molecular weight is characteristic of all types of synthetic polymers. To characterize this distribution, statistical averages are used. The most common of these averages are the "number average molecular weight" (Mn) and the "weight average molecular weight" (Mw).

The number average molecular weight is similar to the standard arithmetic mean associated with a group of numbers. When applied to polymers, the number-average molecular weight refers to the average molecular weight of the molecules in the polymer. The number average molecular weight is figured giving the same amount of significance to each molecule regardless of its individual molecular weight. The number average molecular weight is figured by the following formula where Ni is the number of molecules with a molar mass equal to Mi.

$$\overline{M}_n = \frac{\sum_i N_i M_i}{\sum_i N_i}$$

Slightly different in calculation and much different in meaning is the weight average molecular weight, Mw. The weight average molecular weight is another statistical descriptor of the molecular weight distribution that provides more for significance of larger molecules than the smaller molecules in the distribution. The formula below shows the statistical calculation of the weight average molecular weight.

$$\overline{M}_w = \frac{\sum_i N_i M_i^2}{\sum_i N_i M_i}$$

For GPC, the samples were prepared by diluting in phosphate buffer (per USP monograph method) and analyzed to determine the molecular weight distributions in each sample. The results are summarized below in Tables 10-12. Representative chromatograms from the analysis are presented in FIGS. 3-9.

There are two general reasons for the weight average molecular weight. First, if comparing, for example toughness, the longer molecules influence the toughness of the polymer distribution more so than the shorter molecules do. The weight average molecular weight calculation gives emphasis to these longer molecules, and provides a comparative number that can describe the relative contribution of the long molecules present in a molecular weight distribution. The weight average molecular weight is also a number that is directly correlated to the molecular weight determination of polymers by light scattering, small angle neutron scattering (SANS), and sedimentation velocity.

Secondly, the weight average molecular weight provides insight to the shape of a molecular weight distribution. This value, in connection with the number average molecular weight, provides a ratio determination of the broadness of the molecular weight distribution referred to as the polydispersity index or PI. The PI is defined as the ratio of Mw/Mn. The larger the PI, the more disperse the distribution is. The lowest value that a PI can be is 1. This represents a monodispersed sample—a polymer with all of the molecules in the distribution being the same molecular weight.

Not as commonly referred to, but also provided is the "z-average molecular weight" (Mz). This molecular weight average is a value that further describes the molecular weight distribution. This value can be readily determined from sedimentation equilibrium.

Also sometimes included is the peak molecular weight, Mp. The peak molecular weight value is defined as the mode of the molecular weight distribution. It signifies the molecular weight that is most abundant in the distribution. This value also gives insight to the molecular weight distribution.

Most GPC measurements are made relative to a different polymer standard (usually polystyrene). The accuracy of the results depends on how closely the characteristics of the polymer being analyzed match those of the standard used. The expected error in reproducibility between different series of determinations, calibrated separately, is ca. 5-10% and is characteristic to the limited precision of GPC determinations. Therefore, GPC results are most useful when a comparison between the molecular weight distribution of different samples is made during the same series of determinations.

GPC Precisions and bias are based on statistical data such as an average of measurements, standard deviation, relative percent difference, and/or percent relative standard deviation. For quantitative analyses, the amounts listed in the tables above were referenced to a known amount of standard and are quantitative. Calibration curves were prepared, and relative standard deviation and relative percent difference information are referenced in the report above. For semi-quantitative typical reproducibility as determined by statistical process control of the measurement system is estimated at about 10% (at 95% confidence level, k~2). This reproducibility is an estimate of the uncertainty of a single standard measurement over time, and the uncertainty in a specific measurement must be determined on a case by case basis. For qualitative analyses, analytical reference standards were not analyzed to confirm the presence of the individual components. In such cases it is not possible to assign a numerical value to the "uncertainty" of the matches provided.

Note that samples S1 and S2 contained two peaks with unique molecular weight distributions while sample S3 contained three peaks. Also note that a Mp could not be calculated for "Peak 2" (small molecule peak, likely sucrose) because the peak saturated the detector; samples were analyzed at a concentration which was appropriate for characterization of the higher molecular weight species, with the expense of saturating the detector with the lower molecular weight species of lesser interest.

TABLE 10

Summary of GPC data for sample S1

| SAMPLE DESCRIPTION | PREPARATION | INJECTION | $M_P$ | $M_n$ | $M_W$ | $M_Z$ | PD |
|---|---|---|---|---|---|---|---|
| S1 Peak 1 | 1 | 1 | 28,558 | 23,158 | 33,501 | 49,457 | 1.45 |
|  |  | 2 | 28,558 | 22,954 | 34,613 | 52,469 | 1.51 |
|  | 2 | 1 | 29,137 | 24,149 | 33,976 | 47,218 | 1.41 |
|  |  | 2 | 29,727 | 24,329 | 34,908 | 51,148 | 1.44 |
|  | 3 | 1 | 29,727 | 24,188 | 34,658 | 48,687 | 1.43 |
|  |  | 2 | 29,727 | 24,510 | 34,471 | 47,718 | 1.41 |
|  | Average |  | 29,239 | 23,881 | 34,355 | 49,450 | 1.44 |
|  | Standard Deviation |  | 575 | 655 | 520 | 2,028 | 0.04 |
|  | % RSD |  | 2.0 | 2.7 | 1.5 | 4.1 | 2.6 |
| S1 Peak 2 | 1 | 1 | saturated | 256 | 281 | 306 | 1.10 |
|  |  | 2 | detector; | 256 | 281 | 306 | 1.10 |
|  | 2 | 1 | peak max | 249 | 278 | 307 | 1.12 |
|  |  | 2 | not | 249 | 278 | 307 | 1.12 |
|  | 3 | 1 | available[1] | 251 | 279 | 306 | 1.11 |
|  |  | 2 |  | 251 | 279 | 306 | 1.11 |
|  | Average |  | N/A | 252 | 279 | 306 | 1.11 |
|  | Standard Deviation |  | N/A | 3 | 1 | 1 | 0.01 |
|  | % RSD |  | N/A | 1.3 | 0.5 | 0.2 | 0.8 |

TABLE 11

Summary of GPC data for sample S2

| SAMPLE DESCRIPTION | PREPARATION | INJECTION | $M_P$ | $M_n$ | $M_W$ | $M_Z$ | PD |
|---|---|---|---|---|---|---|---|
| S2 Peak | 1 | 1 | 35,587 | 30,778 | 51,407 | 91,042 | 1.67 |
|  |  | 2 | 34,884 | 31,180 | 50,455 | 83,903 | 1.62 |
|  | 2 | 1 | 35,587 | 31,206 | 51,080 | 86,265 | 1.64 |
|  |  | 2 | 35,587 | 31,442 | 50,835 | 84,143 | 1.62 |
|  | 3 | 1 | 36,303 | 31,997 | 50,985 | 82,454 | 1.59 |
|  |  | 2 | 36,303 | 31,469 | 50,368 | 80,420 | 1.60 |
|  | Average |  | 35,709 | 31,345 | 50,855 | 84,705 | 1.62 |
|  | Standard Deviation |  | 535 | 404 | 392 | 3,660 | 0.03 |
|  | % RSD |  | 1.5 | 1.3 | 0.8 | 4.3 | 1.7 |
|  | 1 | 1 | saturated | 242 | 286 | 327 | 1.18 |
|  |  | 2 | detector; | 243 | 286 | 328 | 1.18 |
|  | 2 | 1 | peak | 241 | 287 | 331 | 1.19 |
|  |  | 2 | max | 240 | 287 | 331 | 1.20 |
|  | 3 | 1 | not | 245 | 286 | 326 | 1.17 |
|  |  | 2 | available | 243 | 288 | 332 | 1.19 |
|  | Average |  | N/A | 242 | 287 | 329 | 1.18 |
|  | Standard Deviation |  | N/A | 2 | 1 | 2 | 0.01 |
|  | % RSD |  | N/A | 0.7 | 0.3 | 0.8 | 0.9 |

TABLE 12

Summary of GPC data for sample S3

| SAMPLE DESCRIPTION | PREPARATION | INJECTION | $M_P$ | $M_N$ | $M_W$ | $M_Z$ | PD |
|---|---|---|---|---|---|---|---|
| S3 Peak 1 | 1 | 1 | 83,090 | 71,378 | 93,965 | 124,983 | 1.32 |
|  |  | 2 | 83,090 | 70,426 | 92,618 | 121,641 | 1.32 |
|  | 2 | 1 | 83,090 | 70,660 | 92,582 | 121,443 | 1.31 |
|  |  | 2 | 83,090 | 70,030 | 92,525 | 123,025 | 1.32 |
|  | 3 | 1 | 83,090 | 70,719 | 92,723 | 121,912 | 1.31 |
|  |  | 2 | 83,090 | 70,627 | 92,615 | 121,900 | 1.31 |
|  | Average |  | 83,090 | 70,640 | 92,838 | 122,484 | 1.31 |
|  | Standard Deviation |  | 0 | 440 | 556 | 1,342 | 0.00 |
|  | % RSD[1] |  | 0.0 | 0.6 | 0.6 | 1.1 | 0.3 |

TABLE 12-continued

Summary of GPC data for sample S3

| SAMPLE DESCRIPTION | PREPARATION | INJECTION | $M_P$ | $M_N$ | $M_W$ | $M_Z$ | PD |
|---|---|---|---|---|---|---|---|
| S3 Peak 2 | 1 | 1 | 6,749 | 4,235 | 6,558 | 9,203 | 1.55 |
| | | 2 | 6,607 | 4,209 | 6,503 | 9,096 | 1.55 |
| | 2 | 1 | 6,607 | 4,179 | 6,492 | 9,135 | 1.55 |
| | | 2 | 6,607 | 4,156 | 6,434 | 8,988 | 1.55 |
| | 3 | 1 | 6,607 | 4,175 | 6,496 | 9,143 | 1.56 |
| | | 2 | 6,607 | 4,162 | 6,488 | 9,140 | 1.56 |
| | Average | | 6,631 | 4,186 | 6,495 | 9,118 | 1.55 |
| | Standard Deviation | | 58 | 30 | 40 | 72 | 0.01 |
| | % RSD[1] | | 0.9 | 0.7 | 0.6 | 0.8 | 0.3 |
| | 1 | 1 | 373 | 305 | 331 | 353 | 1.09 |
| | | 2 | 373 | 310 | 334 | 355 | 1.08 |
| | 2 | 1 | 373 | 334 | 353 | 367 | 1.06 |
| | | 2 | 373 | 342 | 359 | 373 | 1.05 |
| | | 1 | 373 | 342 | 360 | 374 | 1.05 |
| | 3 | 2 | 373 | 344 | 361 | 375 | 1.05 |
| | Average | | 373 | 330 | 350 | 366 | 1.06 |
| | Standard Deviation | | 0 | 17 | 14 | 10 | 0.02 |
| | % RSD[1] | | 0.0 | 5.3 | 3.9 | 2.7 | 1.4 |

Dynamic Light Scattering

PSD analysis was conducted with a laser diffractor. The measurement calculates a volume distribution from the laser diffraction pattern of a cloud of particles. This raw scatter data is then processed with an algorithm and presented on the basis of equivalent spherical diameter. The results have been summarized on a volume (mass) basis in a histogram giving the differential volume percent less and greater than the indicated size.

The particle size analysis was conducted on a Malvern® Zetasizer Nano ZS dynamic light scattering (DLS) instrument. DLS is an ensemble technique that analyzes the light scattered by particles moving in Brownian motion and generates a particle size distribution based on the particle's rate of diffusion. The raw scatter data are processed using a complex algorithm and presented on the basis of an intensity-weighted HYDRODYNAMIC DIAMETER. The analytical technique is summarized in ISO 22412:2008 Particle Size Analysis—Dynamic Light Scattering (DLS) as well as ASTM E2490-09(2015) Standard Guide for Measurement of Particle Size Distribution of Nanomaterials in Suspension by Photon Correlation Spectroscopy (PCS).

The as received samples were water for injection (WFI) and analyzed by DLS to give the overall physical dimension of the particles. The intensity- and volume-weighted results from the analysis are presented in Table 13 and Table 14, respectively.

TABLE 13

Summary of DLS results (intensity weighted)

| SAMPLE | | CUMULANT RESULTS | | NNLS RESULTS[1] | | | | | |
|---|---|---|---|---|---|---|---|---|---|
| | | | | | PEAK 1 | | PEAK 2 | | PEAK 3 |
| ID | REPLICATE | Z-AVERAGE[2] | PDI[3] | PEAK 1 (nm) | WIDTH (nm) | PEAK 2 (nM) | WIDTH (nm) | PEAK 3 (nm) | WIDTH (nm) |
| S1 | Replicate 1 | 13.55 | 0.30 | 17.12 | 10.45 | 2419 | 1460 | no peak | no peak |
| | Replicate 2 | 14.72 | 0.35 | 14.48 | 6.11 | 522.4 | 218.3 | 4668 | 838.3 |
| | Replicate 3 | 17.64 | 0.30 | 16.22 | 6.91 | 705.5 | 425.1 | 4527 | 959.1 |
| | Average | 15.30 | 0.32 | 15.94 | 7.82 | 1215.6 | 701.1 | 4598 | 898.7 |
| S2 | Replicate 1 | 15.76 | 0.32 | 18.79 | 10.60 | 3271 | 1497 | no peak | no peak |
| | Replicate 2 | 15.69 | 0.35 | 16.39 | 7.83 | 1017 | 574.5 | 4213 | 977.6 |
| | Replicate 3 | 14.79 | 0.27 | 18.33 | 11.76 | 4037 | 1136 | 672.2 | 377.2 |
| | Average | 15.41 | 0.31 | 17.84 | 10.06 | 2775 | 1069.2 | 2442.6 | 677.4 |
| S3 | Replicate 1 | 17.35 | 0.22 | 20.9 | 11.18 | 3726 | 1240 | 379.5 | 232.3 |
| | Replicate 2 | 16.17 | 0.20 | 18.43 | 8.10 | 3444 | 1425 | no peak | no peak |
| | Replicate 3 | 17.13 | 0.22 | 20.27 | 9.95 | 3466 | 1276 | 812.4 | 370.1 |
| | Average | 16.88 | 0.21 | 19.87 | 9.74 | 3545.3 | 1313.7 | 596.0 | 301.2 |

[1]NNLS = non-negative least squares data;
[2]Z-average = average particle size distribution;
[3]PDI = polydispersity index

TABLE 14

Summary of DLS results (volume weighted)

| SAMPLE ID | REPLICATE | CUMULANT RESULTS Z-AVERAGE[2] | PDI[3] | PEAK 1 (nm) | PEAK 1 WIDTH (nm) | PEAK 2 (nm) | PEAK 2 WIDTH (nm) | PEAK 3 (nm) | PEAK 3 WIDTH (nm) |
|---|---|---|---|---|---|---|---|---|---|
| S1 | Replicate 1 | 13.55 | 0.30 | 7.94 | 3.89 | 1354 | 455.9 | no peak | no peak |
|  | Replicate 2 | 14.72 | 0.35 | 2.89 | 0.65 | 9.292 | 3.711 | 714.3 | 317.9 |
|  | Replicate 3 | 17.64 | 0.30 | 10.70 | 4.11 | 970.4 | 413.9 | 4904 | 993.8 |
|  | Average | 15.30 | 0.32 | 7.18 | 2.88 | 777.9 | 291.2 | 2809 | 655.9 |
| S2 | Replicate 1 | 15.76 | 0.32 | 8.55 | 4.46 | 1398 | 406.3 | 4450 | 1157 |
|  | Replicate 2 | 15.69 | 0.35 | 8.19 | 4.39 | 1138 | 406.7 | no peak | no peak |
|  | Replicate 3 | 14.79 | 0.27 | 8.88 | 4.21 | no peak | no peak | no peak | no peak |
|  | Average | 15.41 | 0.31 | 8.54 | 4.35 | 1268.0 | 406.5 | 4450 | 1157.0 |
| S3 | Replicate 1 | 17.35 | 0.22 | 11.66 | 5.03 | no peak | no peak | no peak | no peak |
|  | Replicate 2 | 16.17 | 0.20 | 11.61 | 4.62 | 4511 | 1135 | no peak | no peak |
|  | Replicate 3 | 17.13 | 0.22 | 11.66 | 5.03 | 1210 | 430.7 | no peak | no peak |
|  | Average | 16.88 | 0.21 | 11.64 | 4.89 | 2860.5 | 782.9 | no peak | no peak |

[1]NNLS = non-negative least squares data;
[2]Z-average = average particle size distribution;
[3]PDI = polydispersity index Zeta Potential The samples were prepared for zeta potential by diluting in buffer (instrument could not achieve stable readings when diluted in 10 mM NaCl per Nanomaterials 2018, 8, 25). The pH and temperature were recorded at the time of the zeta potential analysis. The results are summarized in Table 6 through Table 8 below. A stable reading could not be obtained for S2. The results for zeta potential testing are reported in Tables 15-17.

TABLE 15

Zeta potential data for sample S1

| SAMPLE ID | ALIQUOT | REP. | ZETA POTENTIAL (mV) | AVG. ZETA POTENTIAL (mV) | ZETA POTENTIAL TEMP (° C.) | pH | pH TEMP (° C.) | CONDUCTIVITY (mS/cm) | AVG. CONDUCTIVITY (mS/cm) | CONDUCTIVITY TEMP (° C.) |
|---|---|---|---|---|---|---|---|---|---|---|
| V1KCJ405 S1 | 1 | 1 | −8.77 | −10.42 | 25 | 10.7 | 25 | 10.0 | 11.2 | 25 |
|  |  | 2 | −8.87 |  |  |  |  | 11.1 |  |  |
|  |  | 3 | −12.2 |  |  |  |  | 11.6 |  |  |
|  |  | 4 | −9.08 |  |  |  |  | 11.7 |  |  |
|  |  | 5 | −13.2 |  |  |  |  | 11.8 |  |  |
|  | 2 | 1 | −10.1 | −9.90 | 25 | 10.69 | 25 | 10.1 | 11.4 | 25 |
|  |  | 2 | −8.86 |  |  |  |  | 11.4 |  |  |
|  |  | 3 | −8.25 |  |  |  |  | 11.7 |  |  |
|  |  | 4 | −11.4 |  |  |  |  | 11.8 |  |  |
|  |  | 5 | −10.9 |  |  |  |  | 11.9 |  |  |

TABLE 16

Zeta potential data for sample S2 (stable reading could not be reached)

| SAMPLE ID | ALIQUOT | REP. | ZETA POTENTIAL (mV) | AVG. ZETA POTENTIAL (mV) | ZETA POTENTIAL TEMP (° C.) | pH | pH TEMP (° C.) | CONDUCTIVITY (mS/cm) | AVG. CONDUCTIVITY (mS/cm) | CONDUCTIVITY TEMP (° C.) |
|---|---|---|---|---|---|---|---|---|---|---|
| V1KCJ405 S2 | 1 | 1 | N/A | N/A | N/A | N/A | N/A | N/A | N/A | N/A |
|  |  | 2 | N/A |  |  |  |  | N/A |  |  |
|  |  | 3 | N/A |  |  |  |  | N/A |  |  |
|  |  | 4 | N/A |  |  |  |  | N/A |  |  |
|  |  | 5 | N/A |  |  |  |  | N/A |  |  |
|  | 2 | 1 | N/A | N/A | N/A | N/A | N/A | N/A | N/A | N/A |
|  |  | 2 | N/A |  |  |  |  | N/A |  |  |

TABLE 16-continued

Zeta potential data for sample S2 (stable reading could not be reached)

| SAMPLE ID | ALIQUOT | REP. | ZETA POTENTIAL (mV) | AVG. ZETA POTENTIAL (mV) | ZETA POTENTIAL TEMP (° C.) | pH | pH TEMP (° C.) | CONDUC-TIVITY (mS/cm) | AVG. CONDUC-TIVITY (mS/cm) | CONDUC-TIVITY TEMP (° C.) |
|---|---|---|---|---|---|---|---|---|---|---|
| | | 3 | N/A | | | | | N/A | | |
| | | 4 | N/A | | | | | N/A | | |
| | | 5 | N/A | | | | | | | |

TABLE 17

Zeta potential data for sample S3

| SAMPLE ID | ALIQUOT | REP. | ZETA POTENTIAL (mV) | AVG. ZETA POTENTIAL (mV) | ZETA POTENTIAL TEMP (° C.) | pH | pH TEMP (° C.) | CONDUC-TIVITY (mS/cm) | AVG. CONDUC-TIVITY (mS/cm) | CONDUC-TIVITY TEMP (° C.) |
|---|---|---|---|---|---|---|---|---|---|---|
| V1KCJ405 S3 | 1 | 1 | −3.35 | −2.972 | 25 | 10.25 | 22.0 | 7.15 | 7.828 | 25 |
| | | 2 | −2.23 | | | | | 7.80 | | |
| | | 3 | −2.13 | | | | | 8.00 | | |
| | | 4 | −3.41 | | | | | 8.08 | | |
| | | 5 | −3.74 | | | | | 8.11 | | |
| | 2 | 1 | −1.78 | | | | | 7.32 | | |
| | | 2 | −3.07 | | | | | 7.99 | | |
| | | 3 | −0.37 | | | | | 8.19 | | |
| | | 4 | −2.53 | | | | | 8.27 | | |
| | | 5 | −3.52 | | | | | 8.29 | | |

Atomic Force Microscopy (AFM)

The as received samples were diluted 50× using MilliQ filtered water (18.2 MO/cm, 4 ppb TOC). About 10 μL of these diluted solutions were deposited onto freshly cleaved pieces of mica and allowed to incubate for about a minute. The samples were then rinsed 5× with MilliQ water and dried with nitrogen. Two 1 μm×1 μm areas were imaged on each sample. The topography differences of these images are presented in colors where the brown is low and the white is high. The z ranges are noted on the vertical scale bar on the right side of the images. Perspective (3-D) views of these surfaces are also included with vertical exaggerations noted in the captions.

Particle size analyses were performed to characterize the heights of the particles present within each area. A height threshold of 0.5 nm was used to identify the particles of interest while excluding non-representative features. The maximum height, minimum height, and mean height results are summarized in Table 18.

TABLE 18

Particle Size Analysis Results

| SAMPLE ID | LOCATION | MEAN HEIGHT (nm) | MINIMUM HEIGHT (nm) | MAXIMUM HEIGHT (nm) | σ | # OF PARTICLES |
|---|---|---|---|---|---|---|
| S1 | 1 | 2.38 | 1.34 | 3.62 | 0.61 | 21 |
| | 2 | 2.43 | 1.16 | 3.73 | 0.73 | 29 |
| S2 | 1 | 3.88 | 0.99 | 8.35 | 1.53 | 84 |
| | 2 | 3.49 | 1.20 | 7.76 | 1.33 | 52 |
| S3 | 1 | 4.20 | 1.19 | 10.19 | 1.46 | 117 |
| | 2 | 3.23 | 0.91 | 7.23 | 1.47 | 49 |
| Blank | 1 | n/a | n/a | n/a | n/a | 0 |

Figure 10:
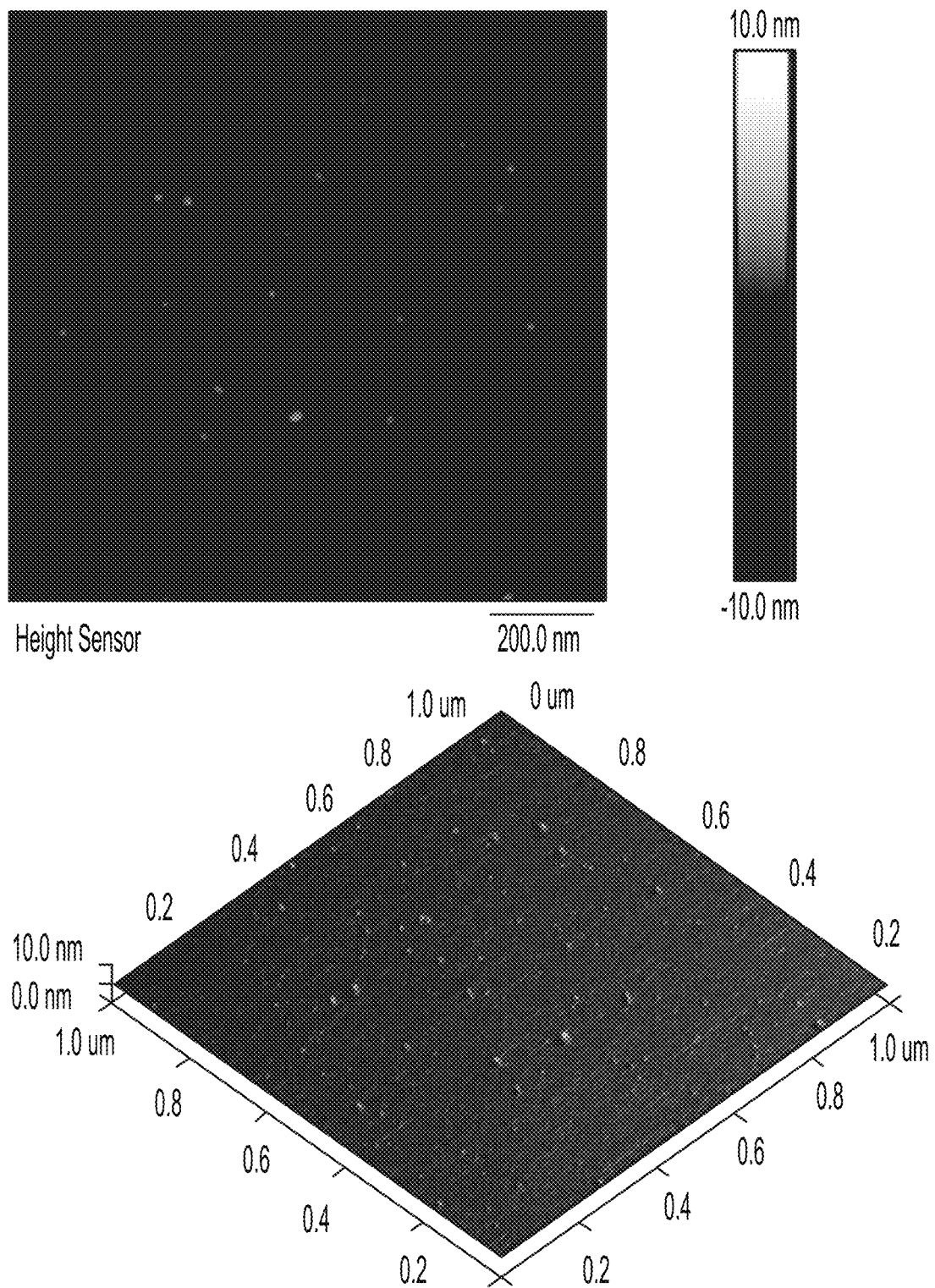
FIG. 10 shows an AFM top and side view for S1.
Figure 11:
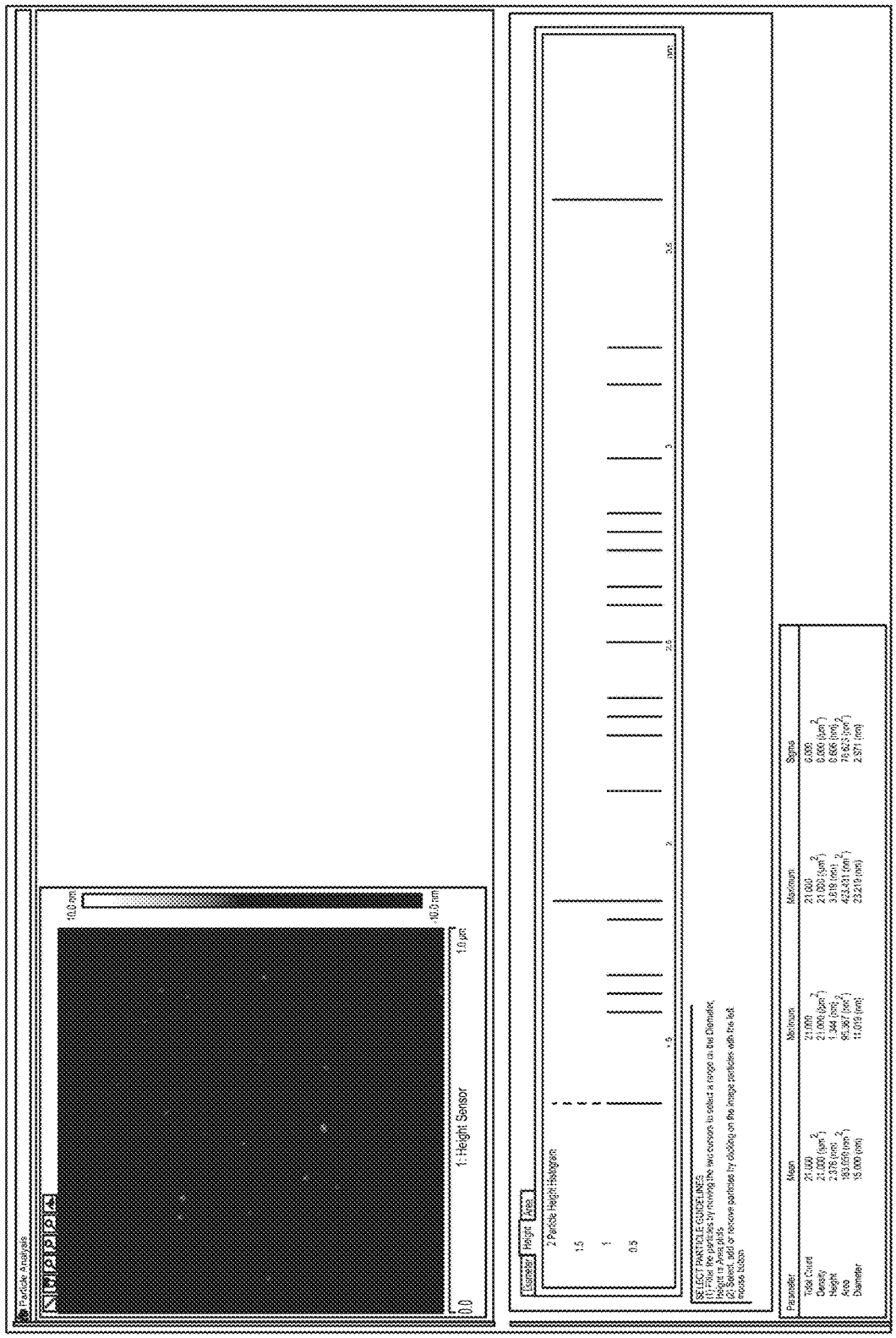
FIG. 11 shows S1, particles size analysis at location 1.
Figure 12:
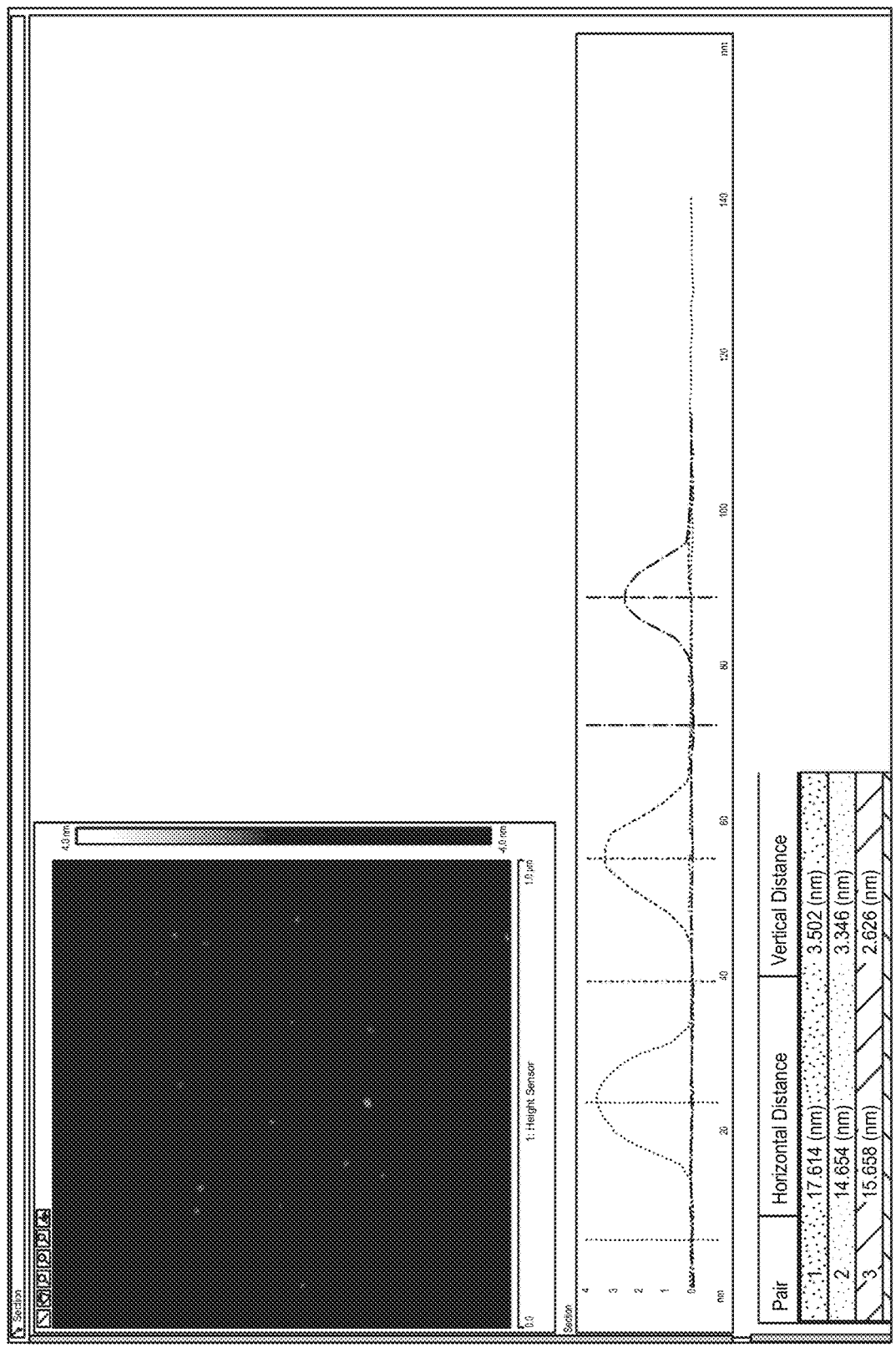
FIG. 12 shows S1, manual section analysis of three particles.

Section analyses were performed to manually measure the heights of representative particles. The Sectional analysis for S1 at location 1 is shown in FIGS. 10, 11, and 12. The results are summarized in Table 19 for each of S1, S2, an S3.

TABLE 19

Particle Size Analysis Results

| SAMPLE ID | LOCATION | PARTICLE 1 HEIGHT (nm) | PARTICLE 2 HEIGHT (nm) | PARTICLE 3 HEIGHT (nm) |
|---|---|---|---|---|
| S1 | 1 | 3.50 | 3.35 | 2.63 |
| | 2 | 3.67 | 2.67 | 2.44 |
| S2 | 1 | 4.96 | 2.68 | 4.77 |
| | 2 | 3.51 | 3.95 | 6.48 |
| S3 | 1 | 3.75 | 6.81 | 3.89 |
| | 2 | 4.37 | 4.27 | 3.81 |

Total Organic Carbon (TOC)

The total organic carbon (TOC) in the samples was calculated by subtracting the inorganic carbon from the total carbon (determined using combustion carbon analyzer). The results are summarized in Table 20 below.

TABLE 20

Calculations for total organic carbon (TOC)

| SAMPLE ID | REPLICATE | TOTAL CARBON (wt %)[1] | AVERAGE TOTAL CARBON | % RSD | TOTAL INORGANIC CARBON | AVERAGE TOTAL CARBON | % RSD[2] | AVERAGE TOTAL ORGANIC CARBON (wt %)[1] |
|---|---|---|---|---|---|---|---|---|
| S1 | Rep 1 | 8.07 | 7.92 | 1.8% | 0.23% | 0.23 | 0.0% | 7.69 |
|  | Rep 2 | 7.89 |  |  | 0.23% |  |  |  |
|  | Rep 3 | 7.79 |  |  | 0.23% |  |  |  |
| S2 | Rep 1 | 12.27 | 12.17 | 0.8% | 0.03% | 0.03 | 0.0% | 12.14 |
|  | Rep 2 | 12.15 |  |  | 0.03% |  |  |  |
|  | Rep 3 | 12.08 |  |  | 0.03% |  |  |  |
| S3 | Rep 1 | 8.56 | 8.69 | 2.5% | <0.03% | <0.03 | — | 8.69 |
|  | Rep 2 | 8.57 |  |  | <0.03% |  |  |  |
|  | Rep 3 | 8.94 |  |  | <0.03% |  |  |  |

[1] wt % = weight percent,
[2] % RSD = Relative Standard Deviation

Osmolality

The osmolality of the samples was measured using vapor pressure method. The vapor pressure method determines osmolality at room temperature with the sample in natural equilibrium. The results of the osmolality test are summarized in Table 21.

TABLE 21

Summary of Osmolality Results

| SAMPLE ID | REPLICATE | OSMOLALITY (mOsm/kg) | AVERAGE OSMOLALITY (mOsm/kg) | % RSD[1] |
|---|---|---|---|---|
| S1 | Replicate 1 | 1539 | 1540 | 0.1% |
|  | Replicate 2 | 1541 |  |  |
|  | Replicate 3 | 1539 |  |  |
| S2 | Replicate 1 | 1677 | 1681 | 0.2% |
|  | Replicate 2 | 1682 |  |  |
|  | Replicate 3 | 1683 |  |  |
| S3 | Replicate 1 | 533 | 529 | 0.7% |
|  | Replicate 2 | 527 |  |  |
|  | Replicate 3 | 526 |  |  |

$Fe^{+3}$ vs $Fe^{+2}$

An aliquot of each sample was diluted into concentrated hydrochloric acid as per the method reference provided by the client, Gupta et al.1 The samples were then analyzed in accordance with the method outlined by Stookey.2 The results are shown in Table 22.

Elemental Screen by Inductively Coupled Plasma/Mass Spectrometry (ICP/MS) and Total Iron and Sodium Content by Inductively Coupled Plasma/Optical Emission Spectroscopy (ICP/OES)

ICP/OES is a spectroscopic technique used to identify and quantify components by element. In ICP, inductive coupling transfers high-frequency energy to a flow of inert gas, which contains the sample as an aerosol. The energy causes the aerosol to vaporize, while exciting the resulting free atoms so that they emit light. The intensity of this light is then related to the concentration of the emitting atoms. This technique requires calibration of the instrument and a second-source calibration verification before, during, and after completion of the analytical run sequence. In addition, instrument blanks follow each check verification standard. This ensures no carry over during the analytical sequence. Concentration measurements of major elements done by ICP have an uncertainty typically in the range from 3 to 5% (at the 95% confidence level). The uncertainty in the concentrations of trace elements might be significantly higher.

Samples S1 through S3 were analyzed by ICP-MS for metals and/or other elements. The samples were also analyzed by ICP-OES to determine total iron and sodium content. Samples were analyzed as received in triplicate. The results are summarized in Table 23-25.

TABLE 22

Summary of iron speciation

| SAMPLE ID | REPLICATE | Fe (II) (mg/mL) | AVERAGE Fe (II) (mg/mL) | % RSD | Fe (III) (mg/mL) | AVERAGE Fe (III) (mg/mL) | % RSD | Fe (REDUCED) (TOTAL IRON, mg/mL) | AVERAGE Fe (III) (mg/mL) | % RSD | % Fe (II) |
|---|---|---|---|---|---|---|---|---|---|---|---|
| S1 | Replicate 1 | 0.43 | 0.41 | 4.3% | 11.20 | 11.43 | 1.8% | 11.70 | 11.87 | 1.3% | 3.4% |
|  | Replicate 2 | 0.41 |  |  | 11.60 |  |  | 12.00 |  |  |  |
|  | Replicate 3 | 0.39 |  |  | 11.50 |  |  | 11.90 |  |  |  |
| S2 | Replicate 1 | 3.16 | 3.16 | 1.6% | 16.80 | 16.90 | 1.0% | 19.90 | 20.03 | 1.2% | 15.8% |
|  | Replicate 2 | 3.21 |  |  | 17.10 |  |  | 20.30 |  |  |  |
|  | Replicate 3 | 3.11 |  |  | 16.80 |  |  | 19.90 |  |  |  |
| S3 | Replicate 1 | 0.45 | 0.44 | 2.0% | 51.70 | 50.90 | 1.7% | 52.20 | 51.33 | 1.8% | 0.8% |
|  | Replicate 2 | 0.43 |  |  | 51.00 |  |  | 51.40 |  |  |  |
|  | Replicate 3 | 0.43 |  |  | 50.00 |  |  | 50.40 |  |  |  |

% RSD = Relative Standard Deviation

TABLE 23

Summary of the elements detected by ICP in S1

| ELEMENT | S1 CONCENTRATION (ppm wt %)[1] REPLICATE 1 | S1 CONCENTRATION (ppm wt %)[1] REPLICATE 2 | S1 CONCENTRATION (ppm wt %)[1] REPLICATE 3 | S1 AVERAGE CONCENTRATION (ppm wt %) |
|---|---|---|---|---|
| Li | <0.1 | <0.1 | <0.1 | <0.1 |
| Be | <0.1 | <0.1 | <0.1 | <0.1 |
| B | 4.2 | 4.1 | 4.1 | 4.1 |
| Na[2] | 1.27% | 1.25% | 1.25% | 1.26% |
| Mg | 0.9 | 0.9 | 0.9 | 0.9 |
| Al | 6.9 | 6.8 | 7.0 | 6.9 |
| Si | 50 | 49 | 51 | 50 |
| P | 2.3 | 2.5 | 2.5 | 2.4 |
| K | 10 | 10 | 10 | 10 |
| Ca | 2 | 1 | <1 | <2 |
| Sc | <0.1 | <0.1 | <0.1 | <0.1 |
| Ti | 0.2 | 0.2 | 0.2 | 0.2 |
| V | 0.4 | 0.4 | 0.4 | 0.4 |
| Cr | 4.6 | 4.4 | 4.6 | 4.5 |
| Mn | 8.4 | 8.5 | 8.7 | 8.5 |
| Fe[2] | 1.07% | 1.07% | 1.07% | 1.07% |
| Co | <0.1 | <0.1 | <0.1 | <0.1 |
| Ni | 1.1 | 1.1 | 1.1 | 1.1 |
| Cu | 0.3 | 0.3 | 0.3 | 0.3 |
| Zn | 1.2 | 1.2 | 1.2 | 1.2 |
| Ga | <0.1 | <0.1 | <0.1 | <0.1 |
| Ge | <0.1 | <0.1 | <0.1 | <0.1 |
| As | 0.2 | 0.2 | 0.2 | 0.2 |
| Se | <0.1 | <0.1 | <0.1 | <0.1 |
| Rb | <0.1 | <0.1 | <0.1 | <0.1 |
| Sr | <0.1 | <0.1 | <0.1 | <0.1 |
| Y | <0.1 | <0.1 | <0.1 | <0.1 |
| Zr | <0.1 | <0.1 | <0.1 | <0.1 |
| Nb | 0.2 | 0.2 | 0.2 | 0.2 |
| Mo | 0.6 | 0.6 | 0.6 | 0.6 |
| Ru | <0.1 | <0.1 | <0.1 | <0.1 |
| Rh | <0.1 | <0.1 | <0.1 | <0.1 |
| Pd | <0.1 | <0.1 | <0.1 | <0.1 |
| Ag | <0.1 | <0.1 | <0.1 | <0.1 |

TABLE 23

Summary of the elements detected by ICP in S1 (cont'd)

| ELEMENT | S1 CONCENTRATION (ppm wt %)[1] REPLICATE 1 | S1 CONCENTRATION (ppm wt %)[1] REPLICATE 2 | S1 CONCENTRATION (ppm wt %)[1] REPLICATE 3 | S1 AVERAGE CONCENTRATION (ppm wt %) |
|---|---|---|---|---|
| Cd | <0.1 | <0.1 | <0.1 | <0.1 |
| In | <0.1 | <0.1 | <0.1 | <0.1 |
| Sn | 0.2 | 0.1 | 0.1 | 0.1 |
| Sb | <0.1 | <0.1 | <0.1 | <0.1 |
| Te | <0.1 | <0.1 | <0.1 | <0.1 |
| Cs | <0.1 | <0.1 | <0.1 | <0.1 |
| Ba | <0.1 | <0.1 | <0.1 | <0.1 |
| La | <0.1 | <0.1 | <0.1 | <0.1 |
| Ce | <0.1 | <0.1 | <0.1 | <0.1 |
| Pr | <0.1 | <0.1 | <0.1 | <0.1 |
| Nd | <0.1 | <0.1 | <0.1 | <0.1 |
| Sm | <0.1 | <0.1 | <0.1 | <0.1 |
| Eu | <0.1 | <0.1 | <0.1 | <0.1 |
| Gd | <0.1 | <0.1 | <0.1 | <0.1 |
| Tb | <0.1 | <0.1 | <0.1 | <0.1 |
| Dy | <0.1 | <0.1 | <0.1 | <0.1 |
| Ho | <0.1 | <0.1 | <0.1 | <0.1 |
| Er | <0.1 | <0.1 | <0.1 | <0.1 |
| Tm | <0.1 | <0.1 | <0.1 | <0.1 |
| Yb | <0.1 | <0.1 | <0.1 | <0.1 |
| Lu | <0.1 | <0.1 | <0.1 | <0.1 |
| Hf | <0.1 | <0.1 | <0.1 | <0.1 |
| Ta | <0.1 | <0.1 | <0.1 | <0.1 |
| W | <0.1 | <0.1 | <0.1 | <0.1 |
| Re | <0.1 | <0.1 | <0.1 | <0.1 |
| Os | <0.1 | <0.1 | <0.1 | <0.1 |
| Ir | <0.1 | <0.1 | <0.1 | <0.1 |
| Pt | <0.1 | <0.1 | <0.1 | <0.1 |

TABLE 23-continued

Summary of the elements detected by ICP in S1 (cont'd)

| ELEMENT | S1 CONCENTRATION (ppm wt %)[1] REPLICATE 1 | S1 CONCENTRATION (ppm wt %)[1] REPLICATE 2 | S1 CONCENTRATION (ppm wt %)[1] REPLICATE 3 | S1 AVERAGE CONCENTRATION (ppm wt %) |
|---|---|---|---|---|
| Au | <0.1 | <0.1 | <0.1 | <0.1 |
| Hg | <0.1 | <0.1 | <0.1 | <0.1 |
| Tl | <0.1 | <0.1 | <0.1 | <0.1 |
| Pb | <0.1 | <0.1 | <0.1 | <0.1 |
| Bi | <0.1 | <0.1 | <0.1 | <0.1 |
| Th | <0.1 | <0.1 | <0.1 | <0.1 |
| U | <0.1 | <0.1 | <0.1 | <0.1 |

TABLE 24

Summary of the elements detected by ICP in S2

| ELEMENT | S2 CONCENTRATION (ppm wt %)[1] REPLICATE 1 | S2 CONCENTRATION (ppm wt %)[1] REPLICATE 2 | S2 CONCENTRATION (ppm wt %)[1] REPLICATE 3 | S2 AVERAGE CONCENTRATION (ppm wt %)[1] |
|---|---|---|---|---|
| Li | <0.1 | <0.1 | <0.1 | <0.1 |
| Be | <0.1 | <0.1 | <0.1 | <0.1 |
| B | 6.8 | 6.8 | 6.8 | 6.8 |
| Na[2] | 0.50% | 0.50% | 0.50% | 0.50% |
| Mg | 1.9 | 1.9 | 1.9 | 1.9 |
| Al | 5.6 | 5.8 | 5.7 | 5.7 |
| Si | 78 | 80 | 79 | 78.5 |
| P | 1 | 1 | 1 | 1 |
| K | 10 | 10 | 10 | 10 |
| Ca | 11 | 12 | 12 | 11.7 |
| Sc | <0.1 | <0.1 | <0.1 | <0.1 |
| Ti | 1.0 | 1.0 | 1.0 | 1 |
| V | <0.1 | <0.1 | <0.1 | <0.1 |
| Cr | <0.1 | <0.1 | <0.1 | <0.1 |
| Mn | <0.1 | <0.1 | <0.1 | <0.1 |
| Fe[2] | 1.77% | 1.76% | 1.77% | 1.77% |
| Co | <0.1 | <0.1 | <0.1 | <0.1 |
| Ni | 0.1 | 0.1 | 0.1 | 0.1 |
| Cu | <0.1 | <0.1 | <0.1 | <0.1 |
| Zn | <0.1 | <0.1 | <0.1 | <0.1 |
| Ga | <0.1 | <0.1 | <0.1 | <0.1 |
| Ge | <0.1 | <0.1 | <0.1 | <0.1 |
| As | <0.1 | <0.1 | <0.1 | <0.1 |
| Se | <0.1 | <0.1 | <0.1 | <0.1 |
| Rb | <0.1 | <0.1 | <0.1 | <0.1 |
| Sr | 0.2 | 0.2 | 0.2 | 0.2 |
| Y | <0.1 | <0.1 | <0.1 | <0.1 |
| Zr | <0.1 | <0.1 | <0.1 | <0.1 |
| Nb | <0.1 | <0.1 | <0.1 | <0.1 |
| Mo | <0.1 | <0.1 | <0.1 | <0.1 |
| Ru | <0.1 | <0.1 | <0.1 | <0.1 |
| Rh | <0.1 | <0.1 | <0.1 | <0.1 |
| Pd | <0.1 | <0.1 | <0.1 | <0.1 |
| Ag | <0.1 | <0.1 | <0.1 | <0.1 |
| Cd | <0.1 | <0.1 | <0.1 | <0.1 |
| In | <0.1 | <0.1 | <0.1 | <0.1 |
| Sn | 0.4 | 0.4 | 0.4 | 0.4 |
| Sb | <0.1 | <0.1 | <0.1 | <0.1 |
| Te | <0.1 | <0.1 | <0.1 | <0.1 |
| Cs | <0.1 | <0.1 | <0.1 | <0.1 |

TABLE 24

Summary of the elements detected by ICP in S2 (cont'd)

| ELEMENT | S2 CONCENTRATION (ppm wt %)[1] REPLICATE 1 | S2 CONCENTRATION (ppm wt %)[1] REPLICATE 2 | S2 CONCENTRATION (ppm wt %)[1] REPLICATE 3 | S2 AVERAGE CONCENTRATION (ppm wt %)[1] |
|---|---|---|---|---|
| Ba | 3.7 | 3.7 | 3.6 | 3.7 |
| La | <0.1 | <0.1 | <0.1 | <0.1 |
| Ce | <0.1 | <0.1 | <0.1 | <0.1 |
| Pr | <0.1 | <0.1 | <0.1 | <0.1 |

TABLE 24-continued

Summary of the elements detected by ICP in S2 (cont'd)

| ELEMENT | S2 CONCENTRATION (ppm wt %)[1] REPLICATE 1 | S2 CONCENTRATION (ppm wt %)[1] REPLICATE 2 | S2 CONCENTRATION (ppm wt %)[1] REPLICATE 3 | S2 AVERAGE CONCENTRATION (ppm wt %)[1] |
|---|---|---|---|---|
| Nd | <0.1 | <0.1 | <0.1 | <0.1 |
| Sm | <0.1 | <0.1 | <0.1 | <0.1 |
| Eu | <0.1 | <0.1 | <0.1 | <0.1 |
| Gd | <0.1 | <0.1 | <0.1 | <0.1 |
| Tb | <0.1 | <0.1 | <0.1 | <0.1 |
| Dy | <0.1 | <0.1 | <0.1 | <0.1 |
| Ho | <0.1 | <0.1 | <0.1 | <0.1 |
| Er | <0.1 | <0.1 | <0.1 | <0.1 |
| Tm | <0.1 | <0.1 | <0.1 | <0.1 |
| Yb | <0.1 | <0.1 | <0.1 | <0.1 |
| Lu | <0.1 | <0.1 | <0.1 | <0.1 |
| Hf | <0.1 | <0.1 | <0.1 | <0.1 |
| Ta | <0.1 | <0.1 | <0.1 | <0.1 |
| W | <0.1 | <0.1 | <0.1 | <0.1 |
| Re | <0.1 | <0.1 | <0.1 | <0.1 |
| Os | <0.1 | <0.1 | <0.1 | <0.1 |
| Ir | <0.1 | <0.1 | <0.1 | <0.1 |
| Pt | <0.1 | <0.1 | <0.1 | <0.1 |
| Au | <0.1 | <0.1 | <0.1 | <0.1 |
| Hg | <0.1 | <0.1 | <0.1 | <0.1 |
| Tl | <0.1 | <0.1 | <0.1 | <0.1 |
| Pb | <0.1 | <0.1 | <0.1 | <0.1 |
| Bi | <0.1 | <0.1 | <0.1 | <0.1 |
| Th | <0.1 | <0.1 | <0.1 | <0.1 |
| U | <0.1 | <0.1 | <0.1 | <0.1 |

TABLE 25

Summary of the elements detected by ICP in S3

| ELEMENT | S3 CONCENTRATION (ppm wt %)[1] REPLICATE 1 | S3 CONCENTRATION (ppm wt %)[1] REPLICATE 2 | S3 CONCENTRATION (ppm wt %)[1] REPLICATE 3 | S3 AVERAGE CONCENTRATION (ppm wt %)[1] |
|---|---|---|---|---|
| Li | <0.1 | <0.1 | <0.1 | <0.1 |
| Be | <0.1 | <0.1 | <0.1 | <0.1 |
| B | 1.0 | 0.9 | 0.9 | 0.9 |
| Na[2] | 0.42% | 0.42% | 0.42% | 0.42% |
| Mg | 1.5 | 1.6 | 1.5 | 1.5 |
| Al | 1.0 | 1.1 | 1.0 | 1.1 |
| Si | 30 | 30 | 30 | 30.0 |
| P | 3 | 3 | 3 | 3.0 |
| K | 3 | 4 | 3 | 3.3 |
| Ca | 3 | 4 | 3 | 3.3 |
| Sc | <0.1 | <0.1 | <0.1 | <0.1 |
| Ti | 0.4 | 0.4 | 0.4 | 0.4 |
| V | 0.1 | 0.1 | 0.1 | 0.1 |
| Cr | 0.3 | 0.2 | 0.2 | 0.2 |
| Mn | <0.1 | <0.1 | <0.1 | <0.1 |
| Fe[2] | 4.50% | 4.52% | 4.52% | 4.51% |
| Co | <0.1 | <0.1 | <0.1 | <0.1 |
| Ni | 0.7 | 0.5 | 0.5 | 0.6 |
| Cu | <0.1 | <0.1 | <0.1 | <0.1 |
| Zn | 0.6 | 0.7 | 0.5 | 0.6 |
| Ga | 0.2 | 0.2 | 0.2 | 0.2 |
| Ge | <0.1 | <0.1 | <0.1 | <0.1 |
| As | <0.1 | <0.1 | <0.1 | <0.1 |
| Se | <0.1 | <0.1 | <0.1 | <0.1 |
| Rb | <0.1 | <0.1 | <0.1 | <0.1 |
| Sr | 0.1 | 0.1 | 0.1 | 0.1 |
| Y | <0.1 | <0.1 | <0.1 | <0.1 |
| Zr | <0.1 | <0.1 | <0.1 | <0.1 |
| Nb | <0.1 | <0.1 | <0.1 | <0.1 |
| Mo | 0.5 | 0.5 | 0.5 | 0.5 |
| Ru | <0.1 | <0.1 | <0.1 | <0.1 |
| Rh | <0.1 | <0.1 | <0.1 | <0.1 |
| Pd | <0.1 | <0.1 | <0.1 | <0.1 |
| Ag | <0.1 | <0.1 | <0.1 | <0.1 |
| Cd | <0.1 | <0.1 | <0.1 | <0.1 |
| In | <0.1 | <0.1 | <0.1 | <0.1 |
| Sn | 2.0 | 1.9 | 1.9 | 1.9 |

TABLE 25-continued

Summary of the elements detected by ICP in S3

| ELEMENT | S3 CONCENTRATION (ppm wt %)[1] REPLICATE 1 | S3 CONCENTRATION (ppm wt %)[1] REPLICATE 2 | S3 CONCENTRATION (ppm wt %)[1] REPLICATE 3 | S3 AVERAGE CONCENTRATION (ppm wt %)[1] |
|---|---|---|---|---|
| Sb | <0.1 | <0.1 | <0.1 | <0.1 |
| Te | <0.1 | <0.1 | <0.1 | <0.1 |
| Cs | <0.1 | <0.1 | <0.1 | <0.1 |
| Ba | 0.5 | 0.5 | 0.5 | 0.5 |
| La | <0.1 | <0.1 | <0.1 | <0.1 |
| Ce | <0.1 | <0.1 | <0.1 | <0.1 |
| Pr | <0.1 | <0.1 | <0.1 | <0.1 |
| Nd | <0.1 | <0.1 | <0.1 | <0.1 |
| Sm | <0.1 | <0.1 | <0.1 | <0.1 |
| Eu | <0.1 | <0.1 | <0.1 | <0.1 |
| Gd | <0.1 | <0.1 | <0.1 | 0.1 |
| Tb | <0.1 | <0.1 | <0.1 | 0.1 |
| Dy | <0.1 | <0.1 | <0.1 | 0.1 |
| Ho | <0.1 | <0.1 | <0.1 | 0.1 |
| Er | <0.1 | <0.1 | <0.1 | 0.1 |
| Tm | <0.1 | <0.1 | <0.1 | 0.1 |
| Yb | <0.1 | <0.1 | <0.1 | 0.1 |
| Lu | <0.1 | <0.1 | <0.1 | 0.1 |
| Hf | <0.1 | <0.1 | <0.1 | 0.1 |
| Ta | <0.1 | <0.1 | <0.1 | 0.1 |
| W | <0.1 | <0.1 | <0.1 | 0.1 |
| Re | <0.1 | <0.1 | <0.1 | 0.1 |
| Os | <0.1 | <0.1 | <0.1 | 0.1 |
| Ir | <0.1 | <0.1 | <0.1 | 0.1 |
| Pt | <0.1 | <0.1 | <0.1 | 0.1 |
| Au | <0.1 | <0.1 | <0.1 | 0.1 |
| Hg | <0.1 | <0.1 | <0.1 | 0.1 |
| Tl | <0.1 | <0.1 | <0.1 | 0.1 |
| Pb | <0.1 | <0.1 | <0.1 | 0.1 |
| Bi | <0.1 | <0.1 | <0.1 | 0.1 |
| Th | <0.1 | <0.1 | <0.1 | 0.1 |
| U | <0.1 | <0.1 | <0.1 | 0.1 |

Fourier Transform Infrared Spectroscopy (FT-IR)

Figure 13:
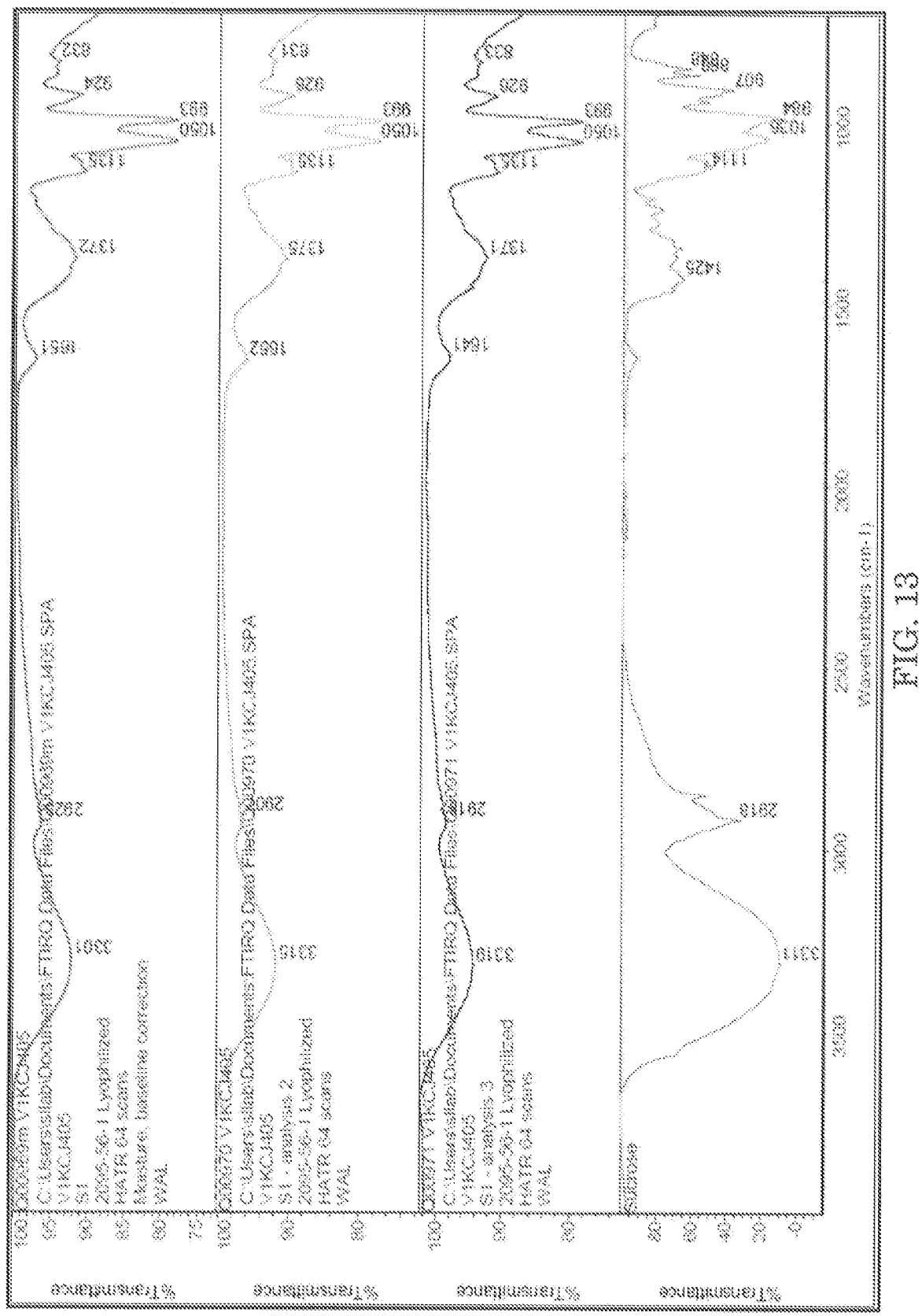
FIG. 13 shows FTIR spectra of S1 and the best library match, sucrose.
Figure 14:
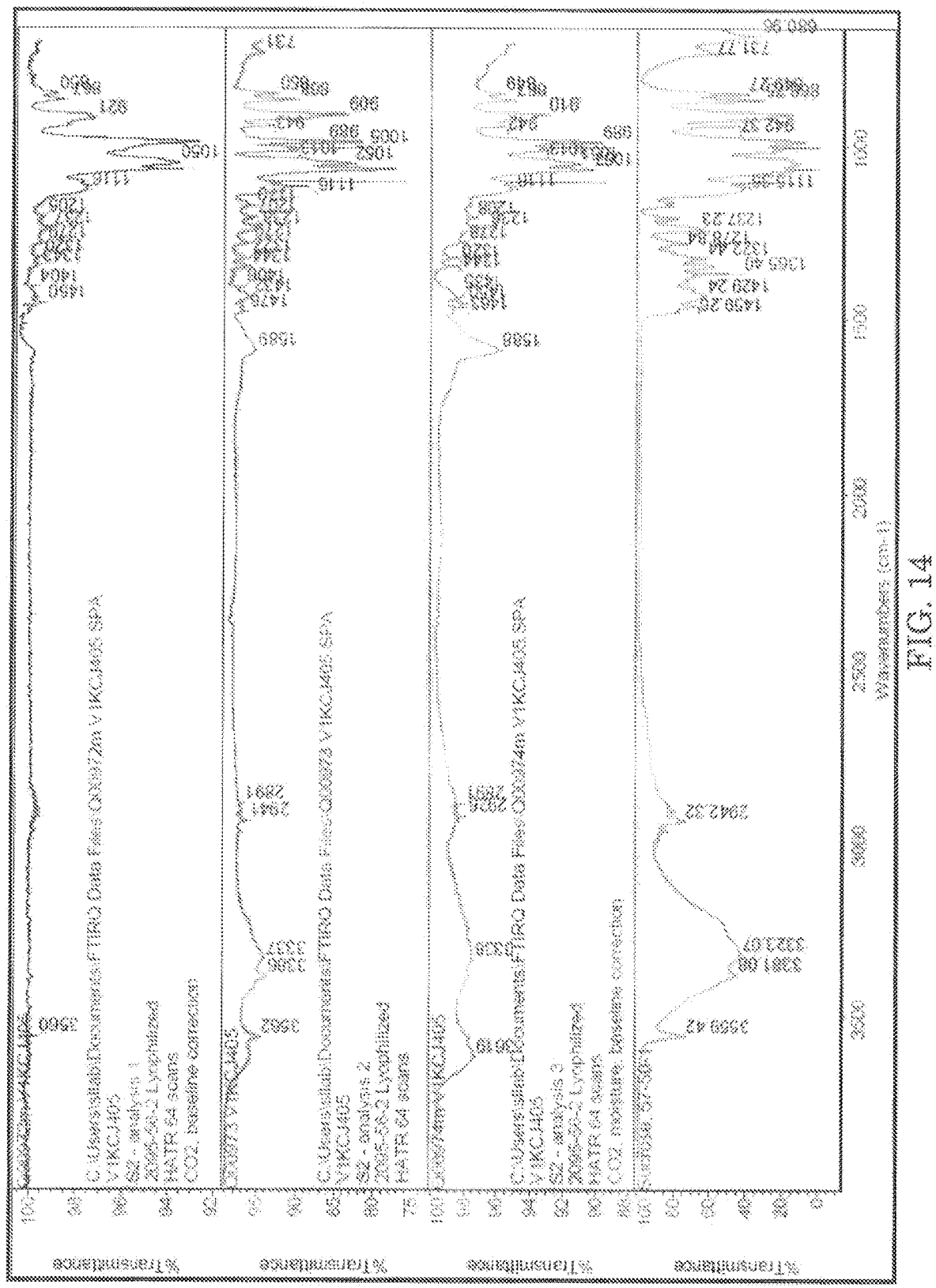
FIG. 14 shows FTIR spectra of S2 and the best library match, sucrose.
Figure 15:
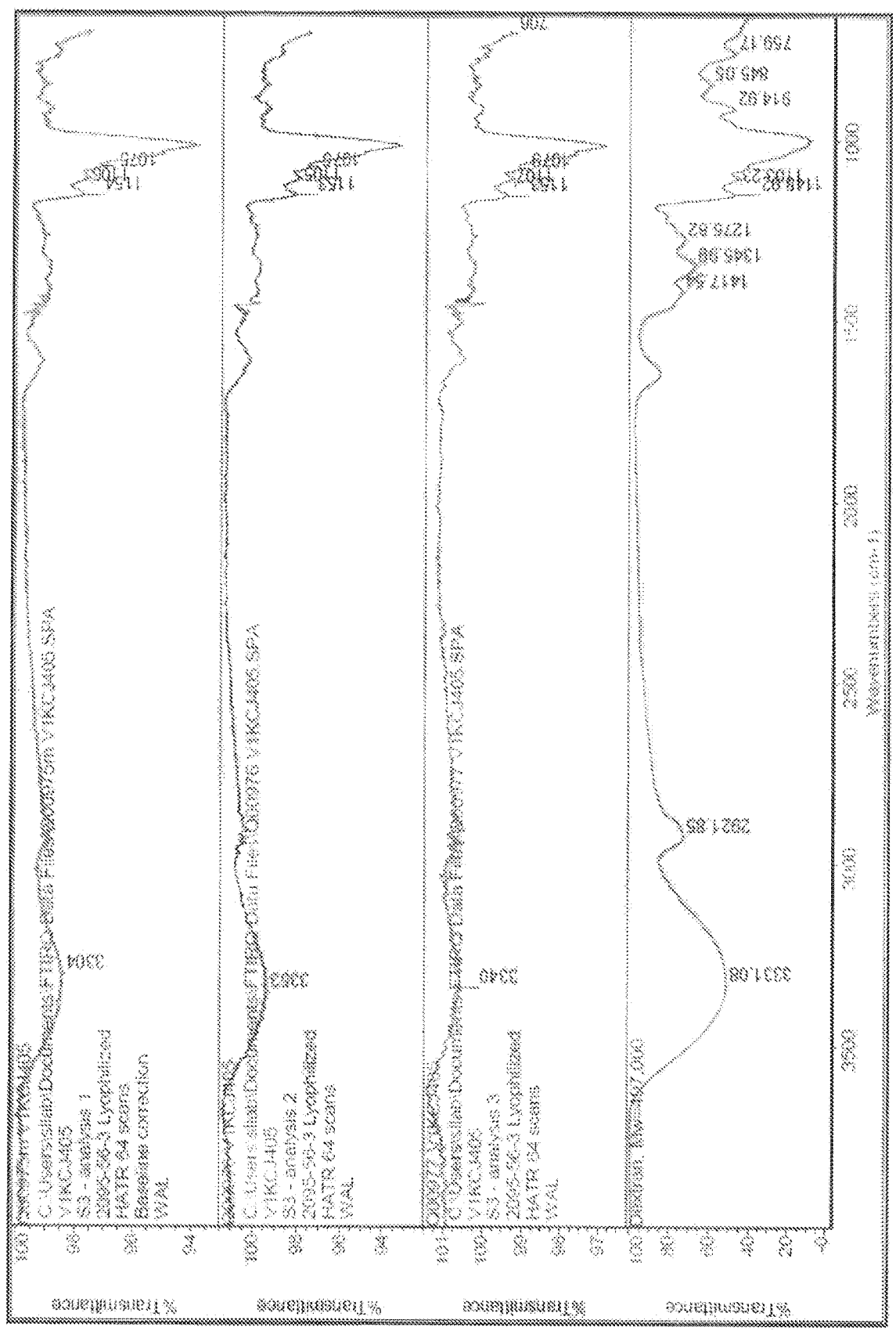
FIG. 15 shows FTIR spectra of S3 and the best library match, dextran.

Fourier Transform Infrared Spectroscopy (FT-IR) is a tool of choice for identification of materials. In FT-IR, the infrared absorption bands are assigned to characteristic functional groups. Based on the presence of a number of such bands, a material under consideration can be identified. Availability of spectra of known compounds increases the probability of making a positive identification. The lyophilized samples were analyzed by Horizontal Attenuated Total Reflectance (HATR), based on the internal reflection of infrared radiation (IR). The FT-IR spectrum of S1 with a spectral library match is presented in FIG. 13 below. The data suggests the material is consistent with sucrose. The FT-IR spectra of S2 and S3 are presented in FIG. 14 and FIG. 15. The assignment of the absorption against functional groups are shown in Table 26-Table 28.

TABLE 26

Characteristic IR Absorption Band Assignments for sucrose in lyophilized S1 preparations

| SUCROSE[3] | LYOPHILIZED S1P1 WAVENUMBERS (cm$^{-1}$) | LYOPHILIZED S1P2 WAVENUMBERS (cm$^{-1}$) | LYOPHILIZED S1P3 WAVENUMBERS (cm$^{-1}$) |
|---|---|---|---|
| OH stretching 3,566-3,263 cm$^{-1}$ | 3,301 cm$^{-1}$ | 3,315 cm$^{-1}$ | 3,319 cm$^{-1}$ |
| C-H stretching 3,014 cm$^{-1}$ | Not detected | Not detected | Not detected |
| CH$_2$ stretching 2,995-2,914 cm$^{-1}$ | 2,923 cm$^{-1}$ | 2,907 cm$^{-1}$ | 2,918 cm$^{-1}$ |
| CH stretching 2,896-2,847 cm$^{-1}$ | Not detected | Not detected | Not detected |
| CH$_2$ deformation, wagging 1,477-1,391 cm$^{-1}$ | Not detected | Not detected | Not detected |
| OH symmetric stretching 1,386 cm$^{-1}$ | 1,372 cm$^{-1}$ | 1,375 cm$^{-1}$ | 1,371 cm$^{-1}$ |
| CH rocking 1,366-1,280 cm$^{-1}$ | Not detected | Not detected | Not detected |
| OH deformation 1,238-1,209, 1,161 cm$^{-1}$ | Not detected | Not detected | Not detected |
| C-C stretching 1,171, 1,073, 1,069, 943, 921 cm$^{-1}$ | 924 cm$^{-1}$ | 926 cm$^{-1}$ | 926 cm$^{-1}$ |

TABLE 26-continued

Characteristic IR Absorption Band Assignments for sucrose in lyophilized S1 preparations

| SUCROSE[3] | LYOPHILIZED S1P1 WAVENUMBERS (cm$^{-1}$) | LYOPHILIZED S1P2 WAVENUMBERS (cm$^{-1}$) | LYOPHILIZED S1P3 WAVENUMBERS (cm$^{-1}$) |
|---|---|---|---|
| CO stretching 1,138-1,087, 1,053-991, 914, 909, 868 cm$^{-1}$ | 1,135, 1,050, 993 cm$^{-1}$ | 1,135, 1,050, 993 cm$^{-1}$ | 1,135, 1,050, 993 cm$^{-1}$ |
| CH$_2$ twisting 850 cm$^{-1}$ | 832 cm$^{-1}$ | 831 cm$^{-1}$ | 833 cm$^{-1}$ |
| C-O stretching 734 cm$^{-1}$ | Not detected | Not detected | Not detected |

TABLE 27

Characteristic IR Absorption Band Assignments for sucrose in lyophilized S2 preparations

| SUCROSE[3] | LYOPHILIZED S2P1 WAVENUMBERS (cm$^{-1}$) | LYOPHILIZED S2P2 WAVENUMBERS (cm$^{-1}$) | LYOPHILIZED S2P3 WAVENUMBERS (cm$^{-1}$) |
|---|---|---|---|
| OH stretching 3,566-3,263 cm$^{-1}$ | 3,560 cm$^{-1}$ | 3,562, 3386, 3,337 cm$^{-1}$ | 3,619, 3,338 cm$^{-1}$ |
| C-H stretching 3,014 cm$^{-1}$ | Not detected | Not detected | Not detected |
| CH$_2$ stretching 2,995-2,914 cm$^{-1}$ | Not detected | 2,941 cm$^{-1}$ | 2,926 cm$^{-1}$ |
| CH stretching 2,896-2,847 cm$^{-1}$ | Not detected | 2,891 cm$^{-1}$ | 2,891 cm$^{-1}$ |
| CH$_2$ deformation, wagging 1,477-1,391 cm$^{-1}$ | 1,450, 1404 cm$^{-1}$ | 1,476, 1,432, 1,406 cm$^{-1}$ | 1,463, 1,450, 1,435 cm$^{-1}$ |
| OH symmetric stretching 1,386 cm$^{-1}$ | Not detected | Not detected | Not detected |
| CH rocking 1,366-1,280 cm$^{-1}$ | 1,343, 1,320, 1,279 cm$^{-1}$ | 1,344, 1,322, 1,279 cm$^{-1}$ | 1,344, 1,320, 1,278 cm$^{-1}$ |
| OH deformation 1,238-1,209, 1,161 cm$^{-1}$ | 1,237, 1,205, 1,161 cm$^{-1}$ | 1,238, 1,207 cm$^{-1}$ | 1,236, 1,208 cm$^{-1}$ |
| C-C stretching 1,171, 1,073, 1,069, 943, 921 cm$^{-1}$ | 1,116, 1,066, 921 cm$^{-1}$ | 1,170, 1,116, 1,067, 943 cm$^{-1}$ | 1,116, 1,067, 942 cm$^{-1}$ |
| CO stretching 1,138-1,087, 1,053-991, 914, 909, 868 cm$^{-1}$ | 1,050, 990 cm$^{-1}$ | 1,052, 1,013, 1,004, 989, 909 cm$^{-1}$ | 1,051, 1,013, 1,004, 989, 910 cm$^{-1}$ |
| CH$_2$ twisting 850 cm$^{-1}$ | 867, 850 cm$^{-1}$ | 868, 850 cm$^{-1}$ | 867, 849 cm$^{-1}$ |
| C-O stretching 734 cm$^{-1}$ | Not detected | 731 cm$^{-1}$ | Not detected |

TABLE 28

Characteristic IR Absorption Band Assignments for sucrose in lyophilized S3 preparations

| DEXTRAN[4] | LYOPHILIZED S3P1 WAVENUMBERS (cm$^{-1}$) | LYOPHILIZED S3P2 WAVENUMBERS (cm$^{-1}$) | LYOPHILIZED S3P3 WAVENUMBERS (cm$^{-1}$) |
|---|---|---|---|
| OH stretching[2] 3,566-,3,263 cm$^{-1}$ | 3,304 cm$^{-1}$ | 3,353 cm$^{-1}$ | 3,340 cm$^{-1}$ |
| Exocyclic CO stretching 1,150 cm$^{-1}$ | 1,154 cm$^{-1}$ | 1,153 cm$^{-1}$ | 1,153 cm$^{-1}$ |
| CO stretching + C-C deformation 1,107 cm$^{-1}$ | 1,106 cm$^{-1}$ | 1,105 cm$^{-1}$ | 1,107 cm$^{-1}$ |
| C-O-C stretching 1,080 cm$^{-1}$ | 1,075 cm$^{-1}$ | 1,075 cm$^{-1}$ | 1,079 cm$^{-1}$ |
| CH stretching 1,018 cm$^{-1}$ | 1,016 cm$^{-1}$ | 1,016 cm$^{-1}$ | 1,015 cm$^{-1}$ |

1H Nuclear Magnetic Resonance Spectroscopy (NMR)

NMR Spectroscopy is an extremely useful method for material characterization. NMR is a physical phenomenon based upon the magnetic property of an atom's nucleus. NMR studies a magnetic nucleus (most commonly that of a hydrogen atom), by aligning it with a very powerful external magnetic field and perturbing this alignment using an electromagnetic pulse. The response to the perturbation is recorded, with each individual nucleus giving a response specific to its chemical, electronic, and spatial environment.

The lyophilized samples were reconstituted in deuterium oxide (D2O) and analyzed by 1H NMR spectroscopy.

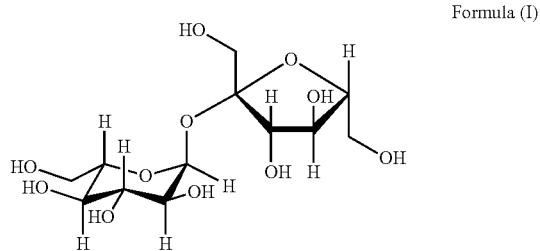

Formula (I)

The structure for sucrose is shown above with hydrogen annotation of Formula (I). The 1H NMR for S1 is shown in Table 29 below:

TABLE 29

Tentative ¹H NMR assignments of S1 in D2O preparations

| ASSIGN-MENTS | CHEMICAL SHIFT (δ ppm) | | | |
|---|---|---|---|---|
| | SUCROSE | S1P1 | S1P2 | S1P3 |
| A | 5.418 | 5.43 | 5.43 | 5.43 |
| B | 4.219 | 4.22 | 4.22 | 4.22 |
| C | 4.055 | 4.06 | 4.07 | 4.06 |
| D | 3.89 | 3.83 | 3.83 | 3.83 |
| E | 3.86 | (broad) | (broad) | (broad) |
| F | 3.826 | | | |
| G | 3.817 | | | |
| J | 3.762 | | | |
| K | 3.679 | 3.69 | 3.69 | 3.69 |
| L | 3.563 | 3.58 | 3.58 | 3.57 |
| M | 3.476 | 3.49 | 3.49 | 3.48 |

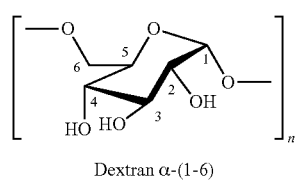

Formula (II)

Dextran α-(1-6)

The structure of dextran is shown above with hydrogen annotation of formula (II). The following Table 30 shows the 1H NMR for S3.

TABLE 30

Tentative ¹H NMR assignments of S3 in D2O

| ASSIGN-MENTS | CHEMICAL SHIFT (δ ppm) | | | |
|---|---|---|---|---|
| | DEXTRAN | S3P1 | S3P2 | S3P3 |
| 1 | 4.99 | 5.01 (shoulder) | 5.01 (shoulder) | 5.00 (shoulder) |
| 2 | 3.58 | 3.60 | 3.61 | 3.60 |
| 4 | 3.52 | (broad) | (broad) | (broad) |
| 3 | 3.74 | 3.77 (broad) | 3.78 (broad) | 3.77 (broad) |
| 5 | 3.92 | 3.97 | 3.97 | 3.97 |
| 6 | 3.99 | (broad) | (broad) | (broad) |

Figure 16:
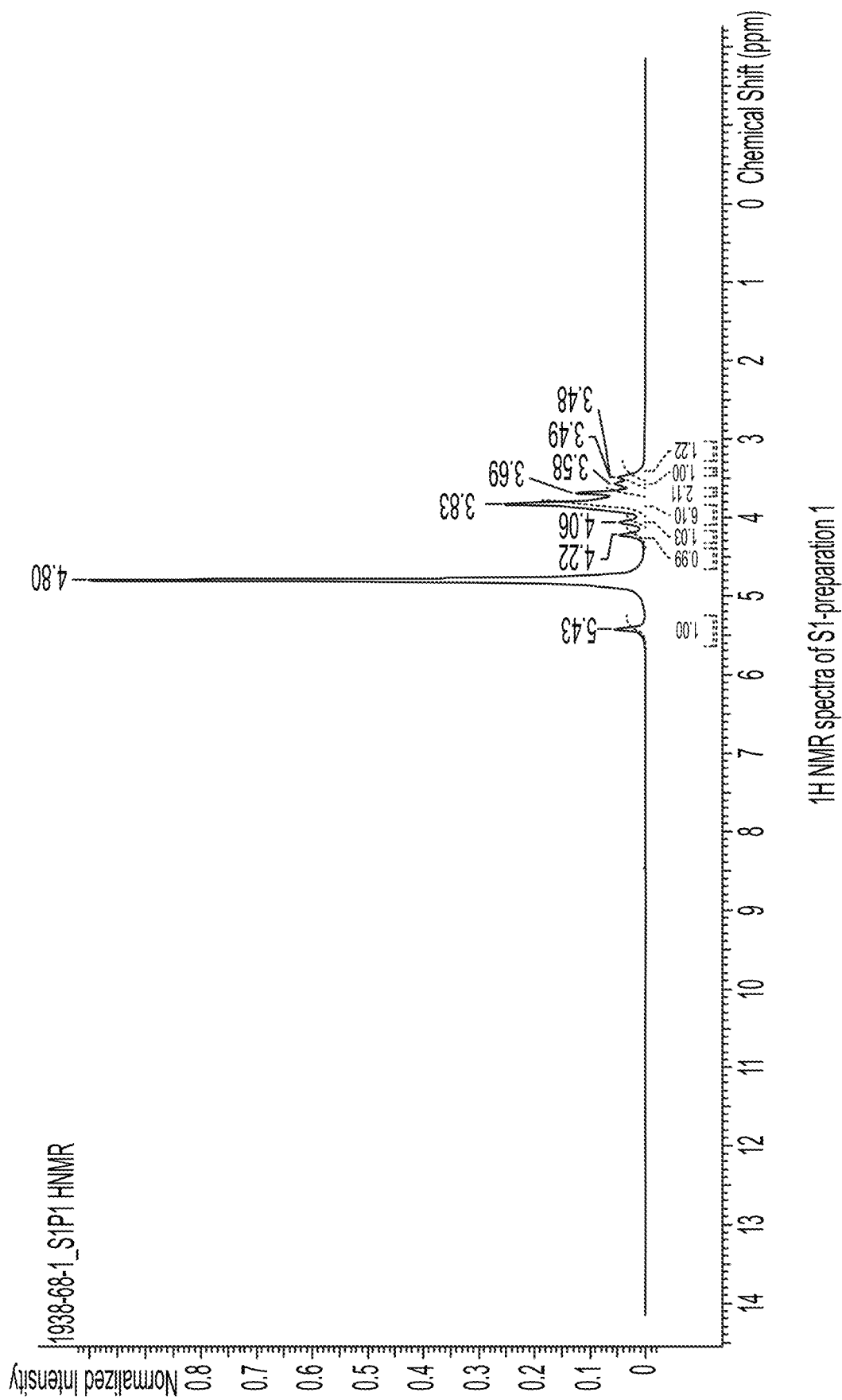
FIG. 16 shows 1H NMR spectra of S1-preparation 1.
Figure 17:
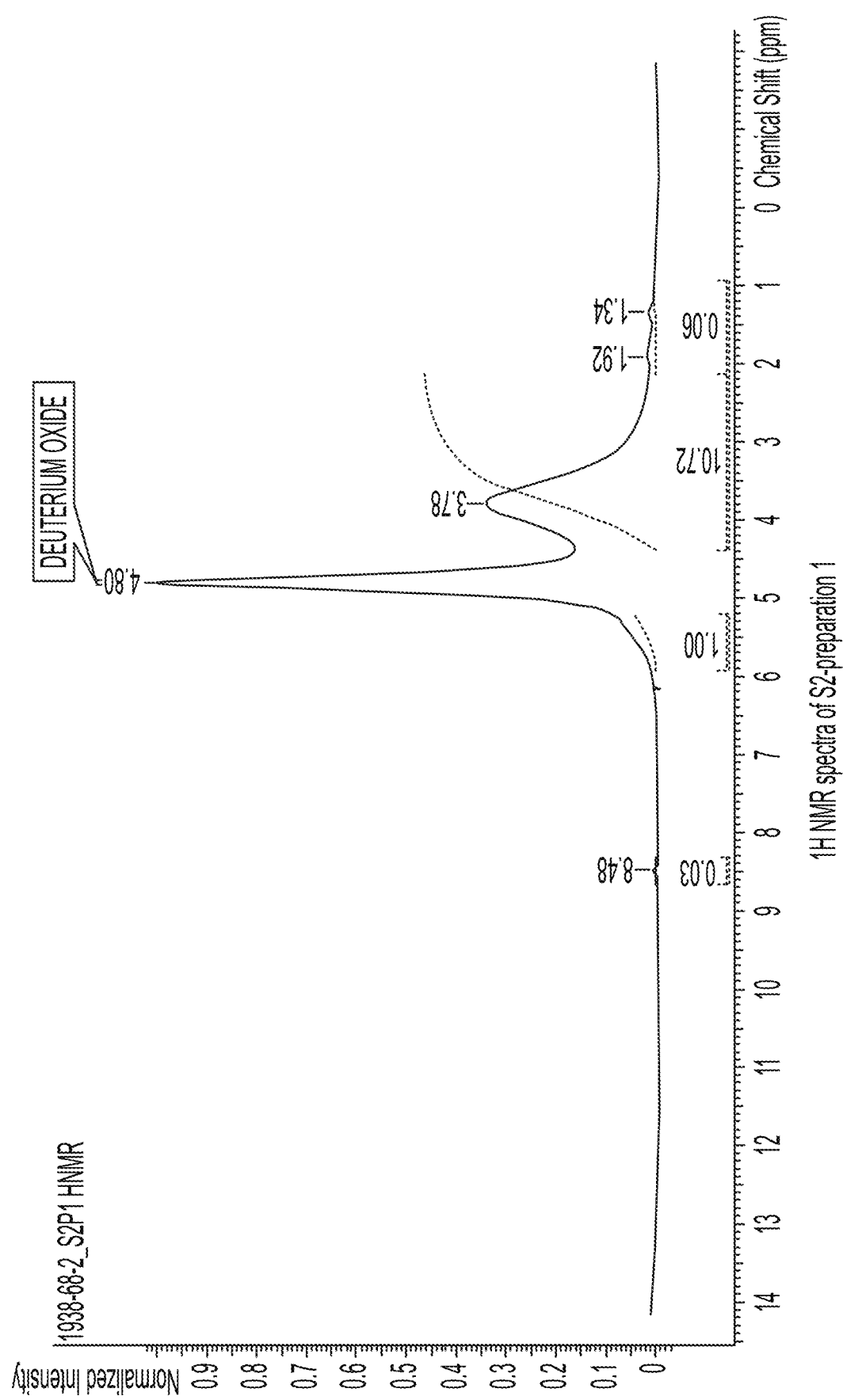
FIG. 17 shows 1H NMR spectra of S2-preparation 1.
Figure 18:
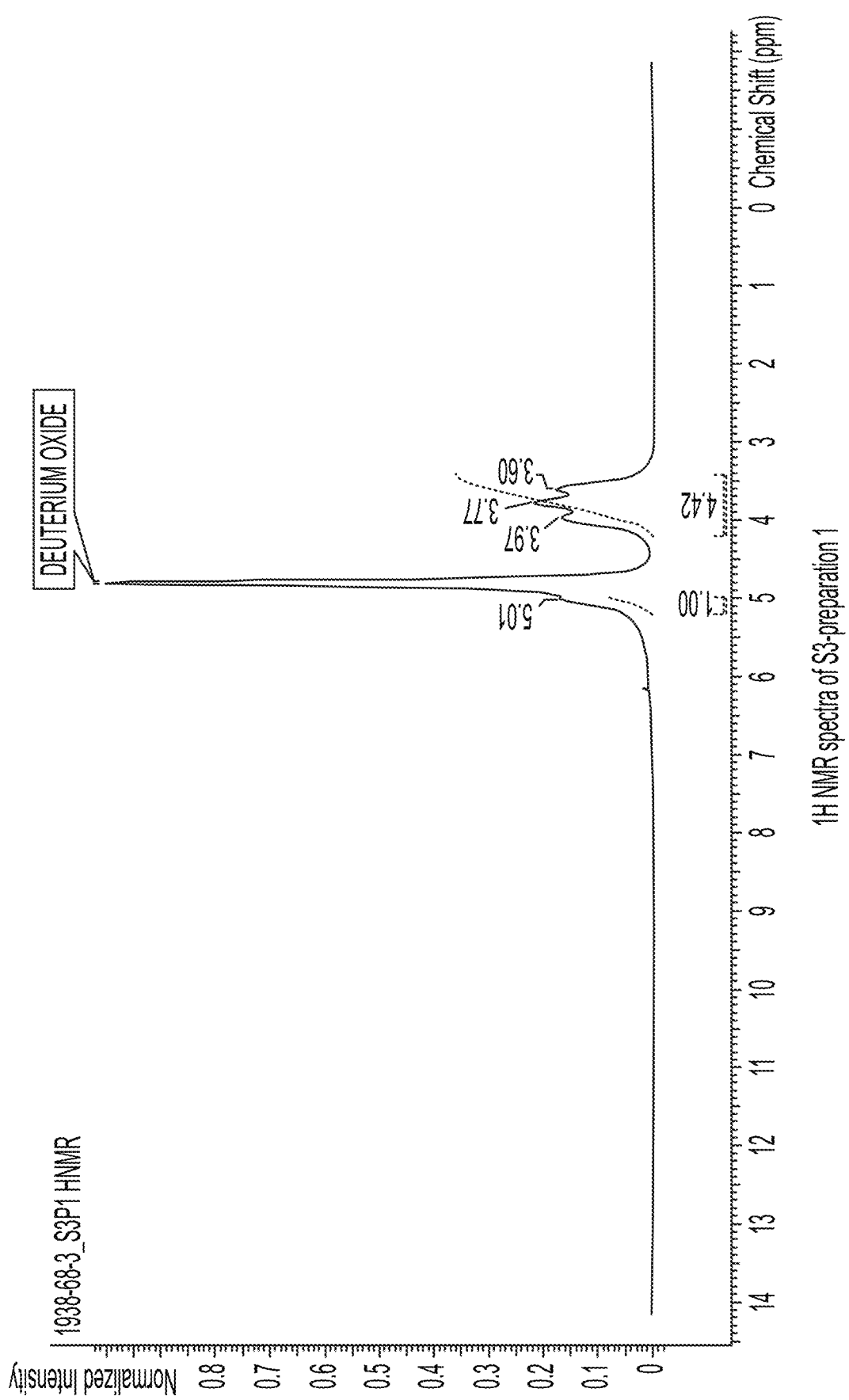
FIG. 18 shows 1H NMR spectra of S3-preparation 1.

The NMR spectra of the prepared samples are presented in FIGS. 16-18. Where possible, tentative assignments for the major chemical shifts observed in the NMR spectra were based on reference spectra of related compounds available in literature.

The data indicates that sucrose is present in sample S1, and the chemical shifts match well with those reported in the literature. However, no peak splitting patterns were observed, which could be due to multiple reasons such as the presence nanoparticulates or the paramagnetic iron itself.

The 1H NMR spectra for sample S2 show a significant amount of peak broadening. It is unknown whether this is due to particulates which create an increased number of chemical environments, or if the nature of the iron in the sample could be responsible for the lack of resolution. Because of the extent of the broadening, no peak assignments could be made. However, the general peak intensities and chemical shifts are consistent with those observed for sucrose, as large broad response was observed from chemical shift 2.5-4.2 ppm, with a slight shoulder visible on the solvent peak near 5.5 ppm.

13C Nuclear Magnetic Resonance Spectroscopy (NMR)

The lyophilized samples were reconstituted in deuterium oxide (D2O) and analyzed by 13C NMR spectroscopy.

Figure 19:
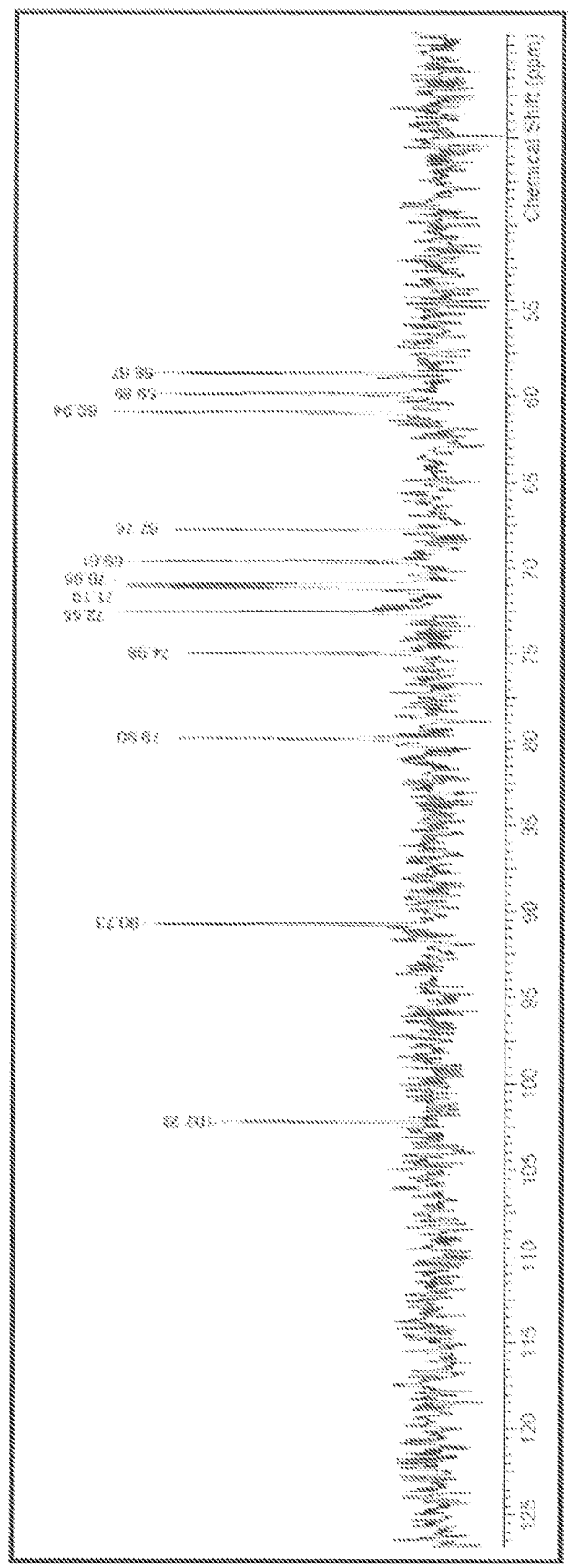
FIG. 19 shows 13C NMR spectra of S1-preparation 1.
Figure 20:
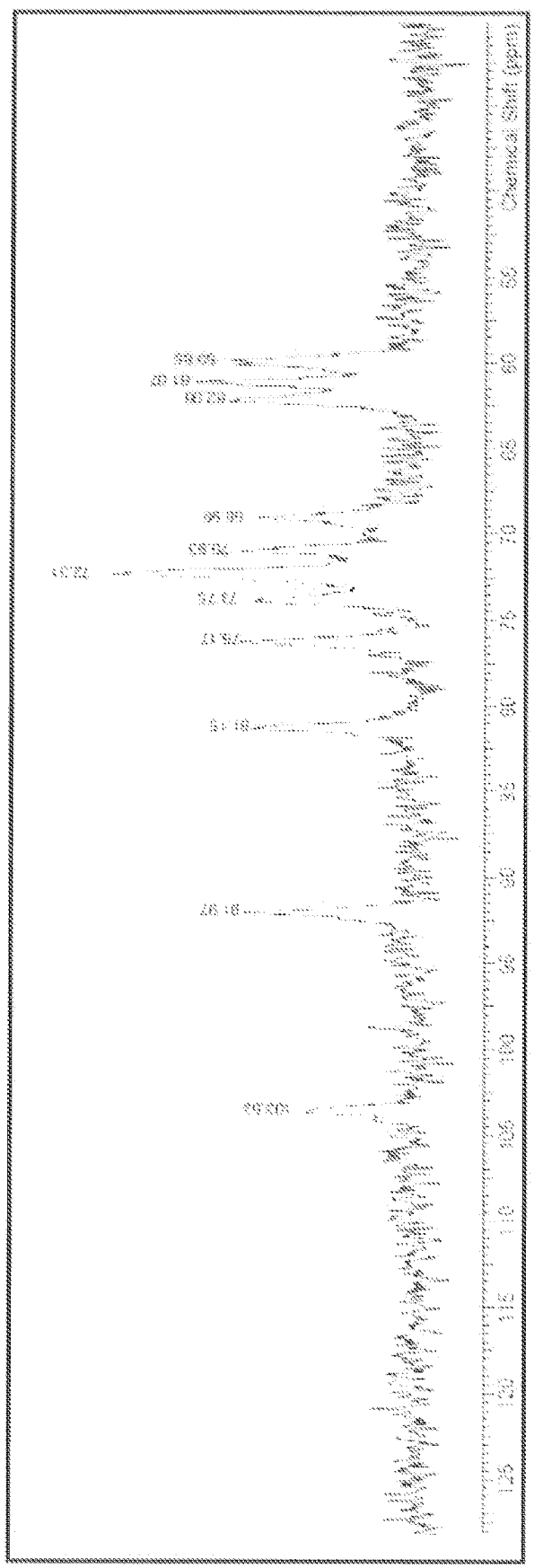
FIG. 20 shows 13C NMR spectra of S2-preparation 1.
Figure 21:
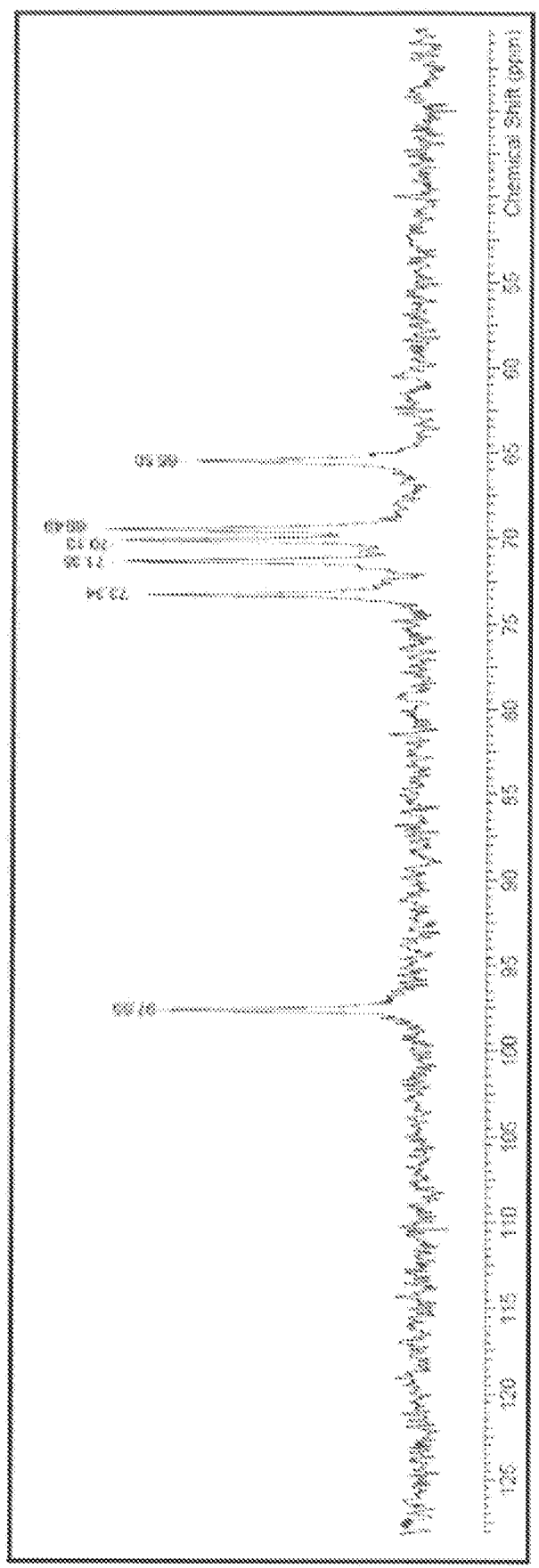
FIG. 21 shows 13C NMR spectra of S3-preparation 1.

The results are summarized in Tables 28-30. The NMR spectra of the prepared samples are presented in FIGS. 19-21. Where possible, tentative assignments for the major chemical shifts observed in the NMR spectra were based on reference spectra of related compounds available in literature.

The data indicates that sucrose is present in sample S1 and S2, and the chemical shifts match well with those reported in the literature. Note that like the proton spectra, sample S2 seemed to have broadening to a greater extent than sample S1. Finally, the peaks observed in sample S3 match well with literature values for dextran, indicating that is it present in the sample.

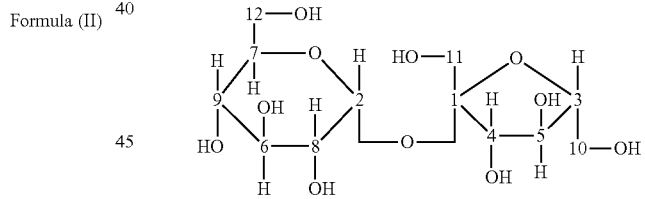

The structure of sucrose is shown above with carbon annotation. The results of 13C NMR are shown in Tables 31 below:

TABLE 31

¹³C NMR assignments of sucrose and S1 in D₂O

| ASSIGN-MENTS | CHEMICAL SHIFT (δ ppm) | | | |
|---|---|---|---|---|
| | SUCROSE | S1P1 | S1P2 | S3P3 |
| 1 | 104.71 | 102.23 | 102.24 | 103.58 |
| 2 | 93.20 | 90.73 | 90.73 | 92.07 |
| 3 | 82.42 | 79.90 | 79.90 | 81.25 |
| 4 | 77.51 | 74.98 | 74.98 | 76.33 |
| 5 | 75.09 | 72.55 | 72.55 | 73.89 |
| 6 | 73.68 | 71.10 | 71.10 | 72.45 |
| 7 | 73.44 | 70.95 | 70.95 | 72.30 |
| 8 | 72.14 | 69.61 | 69.61 | 70.97 |
| 9 | 70.31 | 67.76 | 67.76 | 69.11 |

TABLE 31-continued

13C NMR assignments of sucrose and S1 in D2O

| ASSIGN- | CHEMICAL SHIFT (δ ppm) | | | |
|---|---|---|---|---|
| MENTS | SUCROSE | S1P1 | S1P2 | S3P3 |
| 10 | 63.44 | 60.94 | 60.94 | 62.29 |
| 11 | 62.46 | 59.89 | 59.89 | 61.23 |
| 12 | 61.24 | 58.67 | 58.66 | 60.01 |

TABLE 32

13C NMR assignments of sucrose and S2 in D2O

| ASSIGN- | CHEMICAL SHIFT (δ ppm) | | | |
|---|---|---|---|---|
| MENTS | SUCROSE | S2P1 | S2P2 | S2P3 |
| 1 | 104.71 | 103.53 | 103.71 | 103.69 |
| 2 | 93.20 | 91.97 | 92.19 | 92.23 |
| 3 | 82.42 | 81.15 | 81.42 | 81.38 |
| 4 | 77.51 | 76.17 | 76.41 | 76.28 |
| 5 | 75.09 | 73.75 | 73.98 | 74.01 |
| 6 | 73.68 | | | |
| 7 | 73.44 | | | |
| 8 | 72.14 | 70.93 | 70.97 | 70.97 |
| 9 | 70.31 | 68.99 | 69.38 | 69.14 |
| 10 | 63.44 | 62.06 | 62.34 | 62.29 |
| 11 | 62.46 | 61.07 | 61.36 | 61.16 |
| 12 | 61.24 | 59.85 | 60.11 | 59.98 |

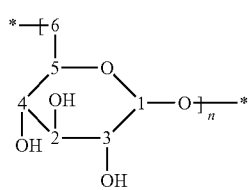

Formula (III)

The structure of dextran is shown above with carbon annotations of formula (III). The following Table 33 shows 13C NMR for dextran of S3 in D2O:

TABLE 33

13C NMR assignments of dextran and S3 in D2O

| ASSIGN- | CHEMICAL SHIFT (δ ppm) | | | |
|---|---|---|---|---|
| MENTS | DEXTRAN | S3P1 | S3P2 | S3P3 |
| 1 | 98.76 | 97.65 | 97.64 | 97.65 |
| 2 | 74.52 | 73.34 | 73.33 | 73.32 |
| 3 | 72.51 | 71.35 | 71.33 | 71.33 |
| 4 | 71.21 | 70.13 | 70.11 | 70.10 |
| 5 | 70.75 | 69.49 | 69.46 | 69.47 |
| 6 | 66.69 | 65.50 | 65.48 | 65.49 |

X-Ray Diffraction (XRD) Analysis (Lyophilized Material)

XRD Analysis is a method by which a crystalline inorganic sample is irradiated with monoenergetic x-rays. The interaction of the lattice structure of the sample with these x-rays is recorded and provides information about the crystalline structure being irradiated. The resulting characteristic "fingerprint" allows for the identification of the crystalline compounds present in the sample. Using a whole-pattern fitting analysis (the Rietveld Refinement), it is possible to perform quantitative analyses on samples containing more than one crystalline compound.

The lyophilized samples were analyzed by XRD to characterize the chemical structure and phases present in the samples. The results from the analysis are presented in Table 34. Note that this sample preparation method resulted in sticky samples for S1 and S2 specifically (S3 was less sticky). For S1 and S2, a drop of methanol was added to the sample and the material was spread flat into the sample holder. Sample S3 was ground in a mortar and pestle.

TABLE 34

XRD phase identification and quantitative analysis for lyophilized samples

| SAMPLE ID | PHASES IDENTIFIED | CONCENTRATION wt %[1] |
|---|---|---|
| S1 | $Na_4Fe_2O_5$-Sodium Iron Oxide Monoclinic, SG: P21/n (14) PDF# 04-013-8809 | 5.2 |
| | Amorphous materials | 94.8 |
| S2 | $C_{12}H_{22}O_{11}$-Sucrose Monoclinic, S.G.: P21 (4) PDF# 02-063-8998 | 42.9 |
| | Amorphous materials | 57.1 |
| S3 | $Na_4Fe_2O_5$-Sodium Iron Oxide Monoclinic, SG: P21/n (14) PDF# 04-013-8809 | 18.8 |
| | Amorphous materials | 81.2 |

Figure 22:
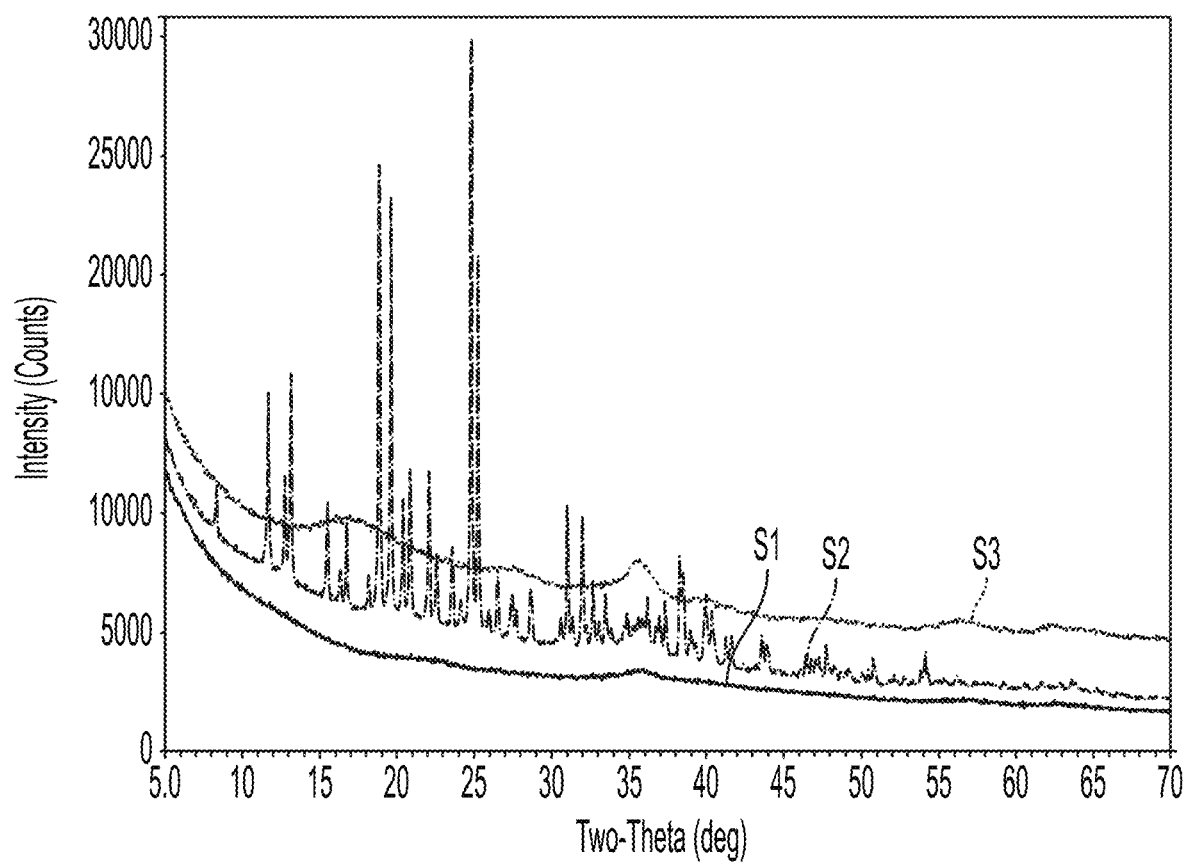
FIG. 22 shows Raw data comparison for the three samples (lyophilized).

FIG. 22 overlays the XRD raw data from the three samples with small offsets for clarity. Sample S2 is different from the other two samples in terms of overall intensities, peak positions as well as peak shape. The broad peak shapes in samples S1 and S3 indicates that these samples consist of a mixture of nano-crystalline and amorphous materials.

Using best matches obtained by comparing the background modelled experimental data to the ICDD/ICSD diffraction database for sample S1, S2, and S3, respectively, Sample S1 and S3 were determined to contain a mixture of amorphous and nano-crystalline materials. The sodium iron oxide reference pattern was superimposed on these experimental data. The markers indicate the location of expected diffraction peaks for each phase and the marker heights indicate the relative peak intensities for a fine-grained, randomly oriented material. Unlike the other two samples, sample S3 is primarily composed of sucrose and amorphous materials.

Semi-quantitative analysis was performed using WPF (whole pattern fitting), which is a subset of Rietveld Refinement that accounts for all areas above the background curve. This technique requires that either the structure factors and atomic locations or the reference intensity ratio (a way of comparing the diffracting power of different phases) are known for all phases identified. During this process, structure factor (which relates to concentration), lattice parameters (which relate to peak position), peak width and peak shape are refined for each phase to minimize the R value—an estimate of the agreement between the model and the experimental data over the entire pattern.

To obtain quantitative results from the sample that contains measurable amounts of amorphous material, the density of the amorphous has to be assigned in order to determine how much amorphous material is present. As a result, the concentration of amorphous material is uncertain. The locations of the amorphous peaks in these samples are assumed to be from the amorphous sucrose which has a density of approximately 1.59 g/cm3. Since WPF attempts to account for everything in the sample, any error in the amorphous concentration will result in errors in the crystalline phases as well. This means that the relative concentrations of the crystalline phases are correct, but the absolute values will be in error by amounts proportional to the error in amorphous concentration.

X-Ray Diffraction (XRD) Analysis (Sugar-Free Material)

The as received samples were diluted in water and placed in a 10000 Da molecular weight cutoff (MWCO) filter and centrifuged to remove the small molecules in the formulation (sugars) which caused amorphous material in the previous XRD analysis. The samples were then washed five more times with water to remove residual small molecules. The resulting material (in capable of passing through the filter) was lyophilized and analyzed by XRD to characterize the chemical structure and phases present in the samples. Note that sample S3 contained two distinct layers following centrifugation, a thick viscous layer and a thinner top layer. These layers were separated and lyophilized separately and analyzed as two samples. The results were averaged to afford the values seen in Table 35, but individual replicates of each layer are presented in the below figures. The results from the analysis are presented in Table

TABLE 35

XRD phase identification and quantitative analysis for samples purified using MWCO filters, then lyophilized

| SAMPLE ID | PHASES IDENTIFIED | CONCENTRATION wt %[1] |
|---|---|---|
| S1 (S1 = S22) | $Fe_{2.67}O_4$-Maghemite Cubic, SG: P4332 (212) PDF# [04-021-3968] | 81.0 |
| | FeOOH-Iron Oxide Hydroxide Orthorhombic PDF# [04-003-2900] | 19.0 |
| S2 (S2 = S23) | $Fe_{2.67}O_4$-Maghemite Cubic, SG: P4332 (212) PDF# [04-021-3968] | 89.9 |
| | FeOOH-Iron Oxide Hydroxide Orthorhombic PDF# [04-003-2900] | 10.1 |
| S3[2] (S3 = S24 and S25) | $Fe_{2.67}O_4$-Maghemite Cubic, SG: P4332 (212) PDF# [04-021-3968] | 74.0 |
| | FeOOH-Iron Oxide Hydroxide Orthorhombic PDF# [04-003-2900] | 26.0 | wt % = weight percent, ±5%;
[2]average of duplicate preparations (two layers observed)

An overlay of the XRD patterns from all four samples (two replicates for S3) is shown in FIG. 23. The patterns are offset for clarity. The phase identification was performed by comparing the best matches between the background-modelled experimental XRD data to the ICDD/ICSD diffraction database for the sample. The reference markers for the phase show where in two-theta the expected experimental peaks should be located and the height of the markers indicates the expected intensity of the experimental peaks, if the sample is fine-grained and randomly oriented. Note that XRD is sensitive to crystal structure but relatively insensitive to elemental or chemical state composition. The phase identification for these samples was difficult due the nanocrystalline nature of the samples which significantly broadens peak in the XRD patterns.

The best matches to the peaks present in all four samples are an iron oxide phase known as maghemite and an iron oxide hydroxide phase. The iron oxide hydroxide phase is atypical as it is formed from the heating of beta phase iron oxide hydroxide to about 300° C. Unfortunately, this reference card does not have the reference intensity ratio (RIR) included which is needed for semi-quantitative analysis. But as the symmetry and compositions are similar to that of the iron oxide hydroxide mineral goethite (alpha-FeOOH), the average RIR of goethite was used for the iron oxide hydroxide for semi-quantitative analysis.

Semi-quantitative analysis was performed using WPF (whole pattern fitting), which is a subset of Rietveld Refinement that accounts for all intensity above the background curve. This technique requires that either the structure factors and atomic locations or the reference intensity ratio (a way of comparing the diffracting power of different phases) are known for all phases identified. During this process, structure factor (which relates to concentration), lattice parameters (which relate to peak position), peak width and peak shape are refined for each phase to minimize the R value—an estimate of the agreement between the model and the experimental data over the entire pattern.

Acid Degradation for Labile Iron (III) Using UV-Visible Spectroscopy

UV/Vis Spectroscopy is used to determine analyte concentration either at one time or often over a desired time period. The technique measures the absorption of light across the ultraviolet and visible light wavelengths through a liquid sample. Samples are dispensed into a small vial and placed between the path of a UV/Vis light and a detector. According to Beer-Lambert's law, with a constant light path length and known absorption coefficient dependent upon wavelength, concentration of a compound in question can be determined from the light absorbed by the sample at that wavelength.

Samples were analyzed using the method adapted from B. S. Barot et al. (2014) which determines the amount of labile iron (III) in the samples using UV-Visible spectroscopy. The results are summarized in Table 36 below.

TABLE 36

Summary of determination of labile iron (III)

| SAMPLE | REPLICATE | LABILE IRON (III) (%) | AVG LABILE IRON (III) (%) | % RSD[1] |
|---|---|---|---|---|
| S1 | 1 | 1.32% | 1.48% | 10.2% |
| | 2 | 1.52% | | |
| | 3 | 1.61% | | |
| S2 | 1 | 2.14% | 2.27% | 5.3% |
| | 2 | 2.38% | | |
| | 3 | 2.30% | | |
| S3 | 1 | 1.40% | 1.34% | 3.7% |
| | 2 | 1.33% | | |
| | 3 | 1.30% | | |

Thermogravimetric Analysis (TGA)

TGA consists of measuring the weight change of a material as a function of temperature in a controlled atmosphere. The technique requires precise measurements of weight, temperature, and temperature change. The resulting thermogram generated from the analysis can determine the content of ingredient classes (e.g., solvents, polymers, inorganic fillers, etc.) and thermal stability of polymers. Precision and bias typical of TGA measurements are discussed under ASTM E2040.

The lyophilized samples were analyzed by Thermogravimetric Analysis (TGA) under nitrogen purge and air purge. Thermal decomposition of the samples occur in three distinct steps as shown in FIG. 24. The results of these steps are summarized in Table 37.

TABLE 37

| | | % WEIGHT LOSS AMBIENT TO 100° C. | % WEIGHT LOSS 100° C. TO 245° C. | % WEIGHT LOSS 245° C. TO 530° C. | % WEIGHT LOSS 530° C. TO 800° C. | % RESIDUE AT 800° C. |
|---|---|---|---|---|---|---|
| ATMOSPHERIC CONDITION | SPECIMEN ANALYZED | | | | | |
| Nitrogen | S1 Specimen | 3.3 | 43.6 | 17.7 | 21.9 | 13.5 |
| Method: | S1 Specimen | 3.3 | 42.3 | 36.4 | 6.6 | 11.4 |
| Ramp | S1 Specimen | 3.6 | 42.1 | 36.4 | 6.9 | 11.0 |
| 10.00° C./min | Average | 3.4 | 42.7 | 30.2 | 11.8 | 12.0 |
| to 800.00° C. | S2 Specimen | 1.1 | 44.9 | 33.1 | 11.2 | 9.7 |
| (N2 purge) | S2 Specimen | 1.0 | 45.3 | 36.3 | 7.6 | 9.8 |
| Isothermal for | S2 Specimen | 1.1 | 44.7 | 36.8 | 7.4 | 10.0 |
| 2.00 | Average | 1.1 | 45.0 | 35.4 | 8.7 | 9.8 |
| min (N2 purge) | S3 Specimen | 2.4 | 8.9 | 42.8 | 23.4 | 22.4 |
| | S3 Specimen | 4.8 | 7.7 | 56.0 | 15.7 | 15.6 |
| | S3 Specimen | 4.0 | 8.1 | 42.4 | 23.4 | 22.0 |
| | Average | 3.7 | 8.2 | 47.1 | 20.8 | 20.0 |
| Air | S1 Specimen | 3.0 | 42.8 | 37.5 | 5.8 | 11.0 |
| Method: | S1 Specimen | 1.9 | 43.8 | 37.2 | 6.0 | 11.0 |
| Ramp | S1 Specimen | 2.5 | 42.9 | 37.6 | 5.4 | 11.5 |
| 10.00° C./min | Average | 2.5 | 43.2 | 37.4 | 5.7 | 11.2 |
| to 800.00° C. | S2 Specimen | 1.1 | 42.8 | 45.0 | 0.6 | 10.5 |
| (Air | S2 Specimen | 0.7 | 43.4 | 45.0 | 0.7 | 10.2 |
| purge) | S2 Specimen | 0.8 | 42.9 | 45.3 | 0.8 | 10.1 |
| Isothermal for | Average | 0.9 | 43.0 | 45.1 | 0.7 | 10.3 |
| 2.00 | S3 Specimen | 4.2 | 8.2 | 63.1 | 2.9 | 21.6 |
| min (Air purge) | S3 Specimen | 4.8 | 7.8 | 63.7 | 2.9 | 20.8 |
| | S3 Specimen | 5.2 | 7.4 | 62.3 | 3.1 | 21.9 |
| | Average | 4.7 | 7.8 | 63.0 | 3.0 | 21.4 |

Differential Scanning Calorimetry (DSC) and Differential Thermal Analysis (DTA)

The lyophilized samples were analyzed by Differential Scanning calorimetry (DSC) under argon purge. Differential Scanning calorimetry (DSC) measures the difference in the heat flows associated with transitions between a sample and an inert reference as a function of temperature and time. Such measurements provide quantitative and qualitative information about physical and chemical changes that involve endothermic or exothermic processes, or changes in heat capacity. See FIG. 25 for DSC thermograms. The summary of DTA is presented in Table 38 below.

TABLE 38

Summary of DTA results

| Atmospheric Condition | Specimen Analyzed | $Texo_1$ (° C.) | $\Delta Hexo_1$ (J/g) | $Texo_2$ (° C.) | Onset Texo2 (° C.) | $\Delta Hexo_2$ (J/g) |
|---|---|---|---|---|---|---|
| Method: | S1 Specimen 1 | 33.2 | 63.8 | 155.8 | 138.2 | 187 |
| Ramp | S1 Specimen 2 | 33.2 | 69.3 | 153.1 | 137.6 | 169 |
| 10.00° C./min | S1 Specimen 3 | 35.1 | 130.9 | 155.9 | 147.3 | 159 |
| to 200.00° C. | Average | 33.8 | 88.0 | 154.9 | 141.0 | 171.7 |
| (N2 purge) | S2 Specimen 1 | 29.2 | 47.6 | 143.5 | 127.1 | 148 |
| | S2 Specimen 2 | n/a | n/a[1] | 142.8 | *[2] | * |
| | S2 Specimen 3 | n/a | n/a | 147.6 | * | * |
| | Average | 29.2 | 47.6 | 127.1 | 127.1 | 148 |
| | S3 Specimen 1 | 38.8 | 117.7 | n/a | n/a | n/a |
| | S3 Specimen 2 | 44 | 45.6 | n/a | n/a | n/a |
| | S3 Specimen 3 | 34.8 | 136.3 | n/a | n/a | n/a |
| | Average | 39.2 | 99.9 | n/a | n/a | n/a | n/a = not observed;
*[2] Possible overlapping transitions

Hydroxide Value by Titration and Determination of Molecular Formula

The as-received sample S1 was titrated in triplicate with 0.00998N HCl to determine the hydroxide value in iron-sucrose injectable solution. The end points of the titrations were pH=7.0. Table 39 summarizes the results of this titration in S1.

Using the assumption that all basic species titrated were from the hydroxide associated with the ferric oxyhydroxide cores, the total number of moles of H+ used in the titration was assumed to be equal to the number of moles of OH—. Considering TOC, and Mw by GPC, the molecular formula of iron sucrose in S1 was calculated as below:

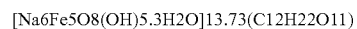

[Na6Fe5O8(OH)5.3H2O]13.73(C12H22O11)

If Mn is considered for this calculation, the molecular formula is:

[Na6Fe5O8(OH)5.3H2O]9.51(C12H22O11)

TABLE 39

Summary of the titration of S1 with 0.01N HCl

| SAMPLE | REPLICATE | MASS OF S1 USED (g) | VOLUME OF 0.00998N HCl (mL) used to reach pH = 7.0 | % RSD[1] |
|---|---|---|---|---|
| S1 | 1 | 1.0020 | 20.87 | 2.1% |
| | 2 | 1.0007 | 21.21 | |
| | 3 | 1.0038 | 20.35 | |
| | Average | 1.0022 | 20.81 | |

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. An aqueous iron pharmaceutical composition comprising:
    iron sucrose;
    bicarbonate; and
    a pharmaceutically acceptable aqueous carrier,
wherein the iron sucrose is present in pharmaceutically effective amount for providing a protective effect to a patient's kidney, the iron being present in both iron (II) and iron (III) form, the pharmaceutical composition has a pH ranging from about 10.5 to about 11.5, a concentration of iron (II) of 0.05% w/v to 0.41% w/v, and the iron sucrose has a Mw according to GPC of between 33,000 and 38,000 Daltons.

2. The aqueous iron composition of claim 1, wherein the composition has a specific gravity between 1.135 and 1.165 at 20° C.

3. The aqueous iron composition of any of claim 1, wherein the composition has a concentration of iron (II) of 0.10% w/v to 0.20% w/v.

* * * * *